US008835835B2

(12) United States Patent
Pevsner

(10) Patent No.: US 8,835,835 B2
(45) Date of Patent: *Sep. 16, 2014

(54) BIOMARKERS OF IONIZING RADIATION

(75) Inventor: Paul H. Pevsner, New York, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/564,849

(22) Filed: Aug. 2, 2012

(65) Prior Publication Data

US 2014/0170682 A1    Jun. 19, 2014

Related U.S. Application Data

(63) Continuation of application No. 12/387,508, filed on May 4, 2009, now Pat. No. 8,269,163.

(60) Provisional application No. 61/126,246, filed on May 3, 2008.

(51) Int. Cl.
*B01D 59/44* (2006.01)
*H01J 49/00* (2006.01)

(52) U.S. Cl.
USPC ............ 250/282; 250/281; 250/287; 250/288; 435/6; 435/7; 435/108.21; 435/194

(58) Field of Classification Search
USPC .................. 250/281, 282, 287, 288; 435/6, 7, 435/108.21, 194
See application file for complete search history.

(56) References Cited

U.S. PATENT DOCUMENTS

| 6,429,018 | B1 | 8/2002 | Cole et al. | |
| 6,869,430 | B2* | 3/2005 | Balbierz et al. | 606/41 |
| 8,269,163 | B2* | 9/2012 | Pevsner | 250/282 |
| 2005/0029444 | A1* | 2/2005 | Caprioli | 250/282 |

OTHER PUBLICATIONS

Rithidech, et al., Experimental Hematology (2007) 35: 117-124.

* cited by examiner

*Primary Examiner* — Jack Berman
*Assistant Examiner* — Meenakshi Sahu
(74) *Attorney, Agent, or Firm* — Klauber & Jackson LLC

(57) ABSTRACT

The present invention provides novel radiation associated markers. The radiation associated markers may be one or more of albumin, LTGF-β, or any protein or peptide listed in any one of Tables 1, 2, 3, 4, 5, and 6 provided herein. The present invention also provides methods of assessing exposure to ionizing radiation by determining the presence of one or more radiation associated markers. The methods may optionally include quantifying one or more of the radiation associated markers. The methods may further include comparing the amount of one or more radiation associated markers in the sample determined to be present in the sample with either (i) the amount determined for temporally matched, normal samples or (ii) the amount determined for samples obtained from individuals or subjects that have not been exposed to an elevated level of ionizing radiation.

5 Claims, 17 Drawing Sheets

2 Gy 33551.1 Da Double
Charge Albumin

10X

63X

3 Gy 33322.7 Da Double Charge
Albumin

2Gy 34573.5 Da LAP

3Gy 34561.2 Da LAP

1Gy 15074.2 Da Hemoglobin
Subunit α

1Gy 72°F Tongue 11427.1 Da
Parathymosin

1Gy 14639.9 Da Fatty Acid-
Binding Protein Adipocyte

2Gy A 14641.9 Da Fatty Acid-
Binding Protein Adipocyte

2Gy 26693.8 Da
Triosphosphate Isomerase

2Gy 15941.1 Da
Superoxide Dismutase

3Gy 15072.2 Da Hemoglobin α
Chains

3Gy BCO11074 NID 52841.2 Da

SEQUENCE LISTING

```
<160> NUMBER OF SEQ ID NOS: 3

<210> SEQ ID NO 1
<211> LENGTH: 10
<212> TYPE: PRT
<213> ORGANISM: Mus musculus

<400> SEQUENCE: 1

Met Ser Gly Pro Arg Lys Ala Pro Glu Asp
1               5                   10

<210> SEQ ID NO 2
<211> LENGTH: 10
<212> TYPE: PRT
<213> ORGANISM: Mus musculus

<400> SEQUENCE: 2

Ala Lys Asp Tyr Tyr Gly Leu Gly Tyr Phe
1               5                   10

<210> SEQ ID NO 3
<211> LENGTH: 9
<212> TYPE: PRT
<213> ORGANISM: Mus musculus

<400> SEQUENCE: 3

Met Arg His Val Gln Ala Glu Leu Ser
1               5
```

BIOMARKERS OF IONIZING RADIATION

CROSS REFERENCE TO RELATED APPLICATIONS

This application is a continuation of U.S. Ser. No. 12/387,508 filed May 4, 2009 now U.S. Pat. No. 8,269,163 which claims priority to U.S. provisional patent application Ser. No. 61/126,246, filed on May 3, 2008, the disclosures of which are herein incorporated by reference in their entirety.

FIELD OF THE INVENTION

This invention relates to new protein biomarkers that may be present after exposure to ionizing radiation and methods of assessing exposure to ionizing radiation as well as diagnostic tests and kits for evaluating exposure to ionizing radiation.

BACKGROUND OF THE INVENTION

Recent work has identified a transcription factor, nuclear factor KAPPA B (NF-KB) which induces the TNF-α encoding gene and activates the cyclooxygenase-2 (COX-2) pathway. At 24 hours post irradiation HIF-1a and COX-2 protein levels were increased. In addition to its well established DNA-damage effects, ionizing radiation induces cell death, and radiation-induced activation of acid sphingomyelinases (ASMases) and the generation of ceramide. Ceramide is generated from sphingomyeline by the action of a neutral or ASMase or by de novo synthesis coordinated through the enzyme ceramidesynthase. Once generated, ceramide may serve as a second messenger molecule in signaling responses to physiologic or environmental stimuli, or it may be converted to a variety of structural or effector molecules. With a single dose of 3 Gy, there is activation of protein kinase B/AKT (PKB/AKT) signaling. Within minutes of irradiation, phosphorylation of the serine/threonin protein kinase PKB/AKT at serine-residue 473 appears. This activation of PKB/AKT contributes to inhibit glycogen synthase kinase-3beta (GSK3beta), which has a clear inhibitory role in endothelial cell survival.

One problem first responders face in the event of a nuclear disaster is to rapidly and efficiently identify victims that need medical treatment and determine what level of treatment is appropriate. It is a priority to minimize time to diagnosis to identify patient treatment needs, minimize the time required for emergency technicians (ET) provide diagnosis, minimize the number of interactions with the patient, minimize system stockpile cost, minimize the dependence on infrastructure (communications, transport, etc.), minimize the needs for trained personnel to administer tests, and uniquely identify patient and diagnostic results.

Simple, quick test strips that change color, like the ones used for sugar or albumin by diabetics, are currently available. They are used without medical or other highly trained personal or expensive equipment. It would be highly desirable to provide such a simple test strip that changes color that could be used as evidence of ionizing radiation (IR) exposure. A positive test that could be used to identify a person who has been exposed to radioactive material has many applications.

SUMMARY OF THE INVENTION

In a first aspect, the present invention provides novel radiation associated markers. The radiation associated markers may be one or more of albumin, LTGF-β, or any protein or peptide listed in any one of Tables 1, 2, 3, 4, 5, and 6 provided herein.

In a second aspect, the present invention provides methods of assessing exposure to ionizing radiation by determining the presence of one or more radiation associated markers. The radiation associated markers may be one or more of albumin, LTGF-β, or any protein or peptide listed in any one of Tables 1, 2, 3, 4, 5, and 6 provided herein.

The sample used for determining the presence of one or more radiation associated markers may be, for instance, saliva, a buccal swab, amniotic fluid, plasma, serum, urine or blood. The one or more radiation associated markers may be identified by many methods well known to those of skill in the art including Matrix assisted laser desorption ionization (MALDI) mass spectrometry. The radiation associated markers may also be identified by contacting the sample with an antibody which specifically binds to the radiation associated marker under conditions permitting formation of a complex between the antibody and the radiation associated marker, and optionally measuring the amount of complexes formed, thereby determining the amount of the radiation associated marker.

The methods may optionally include quantifying one or more of the radiation associated markers. The methods may further include comparing the amount of one or more radiation associated markers in the sample determined to be present in the sample with either (i) the amount determined for temporally matched, normal samples or (ii) the amount determined for samples obtained from individuals or subjects that have not been exposed to an elevated level of ionizing radiation. The relative absence of one or more of the radiation associated markers in the sample indicates that the individual has not been exposed to an elevated level of ionizing radiation, and the relative abundance of one or more of the radiation associated markers in the sample indicates that the individual has been exposed to an elevated level of ionizing radiation. In some embodiments, one or more of the radiation associated markers are not present in detectable levels in normal tissue unaffected by elevated levels of ionizing radiation at all. In other embodiments, one or more of the radiation associated markers is present in levels that are 10%, 20%, 30%, 50%, 75% or more greater than the amount of the corresponding radiation associated marker in normal tissue unaffected by elevated levels of ionizing radiation at all. In still other embodiments, one or more of the radiation associated markers is present in levels that are 2×, 3×, 4×, 5×, 10×, 25×, 50×, 100×, 1,000×, or even 10,000× or more greater than the amount of the corresponding radiation associated marker in normal tissue unaffected by elevated levels of ionizing radiation at all.

In some embodiments, the elevated levels of ionizing radiation may be 10%, 20%, 30%, 50%, 75% or more greater than the amount of ionizing radiation experienced normally from environmental sources. In still other embodiments, the elevated levels of ionizing radiation may be 2×, 3×, 4×, 5×, 10×, 25×, 50×, 100×, 500×, 1,000×, 5,000×, 10,000× 100,000×, 1,000,000× or more greater than the amount of ionizing radiation experienced normally from environmental sources.

The methods of the present invention are applicable to determining the relative amount of ionizing radiation to which an individual has been exposed. Likewise, the methods of the present invention are applicable to determining the relative amount of damage caused by ionizing radiation to an individual. The relative amount of ionizing radiation to which an individual has been exposed and the relative amount of damage caused by ionizing radiation to an individual may be determined, for instance, by quantifying the amount of one or more radiation associated marker present in a tissue or by determining the presence of one or more radiation associated marker that is not present in a tissue until a particular threshold of ionizing radiation is experience or until a particular threshold of damage to a tissue is crossed.

In a third aspect, the present invention further provides a method of predicting outcome in a subject after exposure to elevated levels of ionizing radiation. In some embodiments, it is a method of predicting the likelihood of surviving long term after exposure to elevated ionizing radiation. In other embodiments, it is a method of predicting the relative amount of damage caused to an individual or to a tissue by exposure to elevated ionizing radiation comprising determining the presence or the relative presence as compared to normal samples or normal subjects of one or more radiation associated markers. One, two, three, or more of the radiation associated markers may be present in the sample and may be identified. One, two, three, or more of the radiation associated markers may be present in the sample and may be elevated in comparison to samples obtained from individuals that have not been exposed to elevated levels of ionizing radiation.

The sample used for determining the presence of one or more radiation associated markers may be, for instance, saliva, plasma, serum, urine or blood. The one or more radiation associated markers may be identified by many methods well known to those of skill in the art including Matrix assisted laser desorption ionization (MALDI) mass spectrometry. The radiation associated markers may also be identified by contacting the sample with an antibody which specifically binds to the radiation associated marker under conditions permitting formation of a complex between the antibody and the radiation associated marker, and optionally measuring the amount of complexes formed, thereby determining the amount of the radiation associated marker in the sample.

The methods may optionally include quantifying one or more of the radiation associated markers. The methods may further include comparing the amount of radiation associated markers in the sample determined to be present in the sample with either (i) the amount determined for temporally matched, normal samples or (ii) the amount determined for samples obtained from individuals that have not been exposed to elevated levels of ionizing radiation. The relative absence of one or more of the radiation associated markers in the sample indicates that the likelihood of significant damage, death, illness or medical complications is relatively low, and the relative abundance of one or more of the radiation associated markers in the sample indicates that the likelihood of significant damage, death, illness or medical complications is relatively high.

The invention provides methods for determining the relative likelihood of significant damage, death, illness or medical complications comprising the steps of: (a) obtaining a biological sample from an individual; (b) measuring an amount of one or more radiation associated markers present in the biological sample; and (c) comparing the amount of one or more radiation associated markers with a predetermined value, whereby the amount of radiation associated markers relative to the predetermined value indicates the likelihood of significant damage, death, illness or medical complications or the relative likelihood of a positive or negative medical outcome.

The methods of the invention can be used alone or in combination with any known test for determining the relative likelihood of significant damage, death, illness or medical complications or for determining the prognosis of exposure to ionizing radiation, including, but not limited to, X-Ray, ultrasound, CAT scan, and other blood marker analysis. The methods of the invention may be used to screen a biological sample collected at any time either before or after a first exposure to elevated levels of ionizing radiation has occurred.

In a fourth aspect, the present invention further provides a method of determining the amount of radiation therapy that has been delivered to a particular tissue. In other embodiments, it is a method of predicting the relative amount of damage caused to a particular tissue by exposure to elevated ionizing radiation from radiation therapy comprising determining the presence or the relative presence as compared to normal samples or normal subjects of one or more radiation associated markers. One, two, three, or more of the radiation associated markers may be present in the tissue and may be identified. One, two, three, or more of the radiation associated markers may be present in the tissue and may be elevated in comparison to tissues that have not received radiation therapy.

In a fifth aspect, the present invention provides a kit for assessing the likelihood of significant damage, death, illness or medical complications post exposure to elevated levels of ionizing radiation by determining the presence or absence or by quantifying the amount of one or more radiation associated markers. The kits may contain biomarker identification and bioassay systems that address both the problem of a very rapid and inexpensive Point of Care (POC) diagnostic determination of radiation exposure and of quantitative High Throughput (FIT) diagnostic determination of radiation exposure. The kits and bioassay systems are useful as a means for making a rapid diagnosis and a quantitative high throughput diagnosis. The kits and bioassay systems utilize biochemistry that serves as the basis for assay systems based on one or more biomarkers indicative of a dose or ionizing radiation received. Immunoassays may be provided to quantitatively measure radiation dose. These immunoassays may be incorporated into commercial diagnostic systems using both an established strip test technology to provide a >2 Gy screening diagnosis for quick triage and microfluidics technology that provides a low cost high throughput quantitation capability to indicate dosing level at +/−0.5 Gy to determine the course of treatment to be received. Examples of such microfluidics devices include a handheld microfluidic reader available from Claros Diagnostics, Inc.

The kits and bioassays use identified biomarkers. Commercial antibodies may be obtained or immunoassays developed to provide a quantitative measure of the biomarkers. The commercial antibodies or immunoassays may be embedded into a test strip using established technology. These test strips may provide, for instance, a 0-5 or 0-2 Gy quantitative screening diagnosis for quick triage. In some embodiments, the test strips may change color to provide a useful gauge of the amount of elevated ionizing radiation to which a tissue or an individual has been exposed or to gauge the amount of damage a tissue or an individual has experienced.

Figure 4:
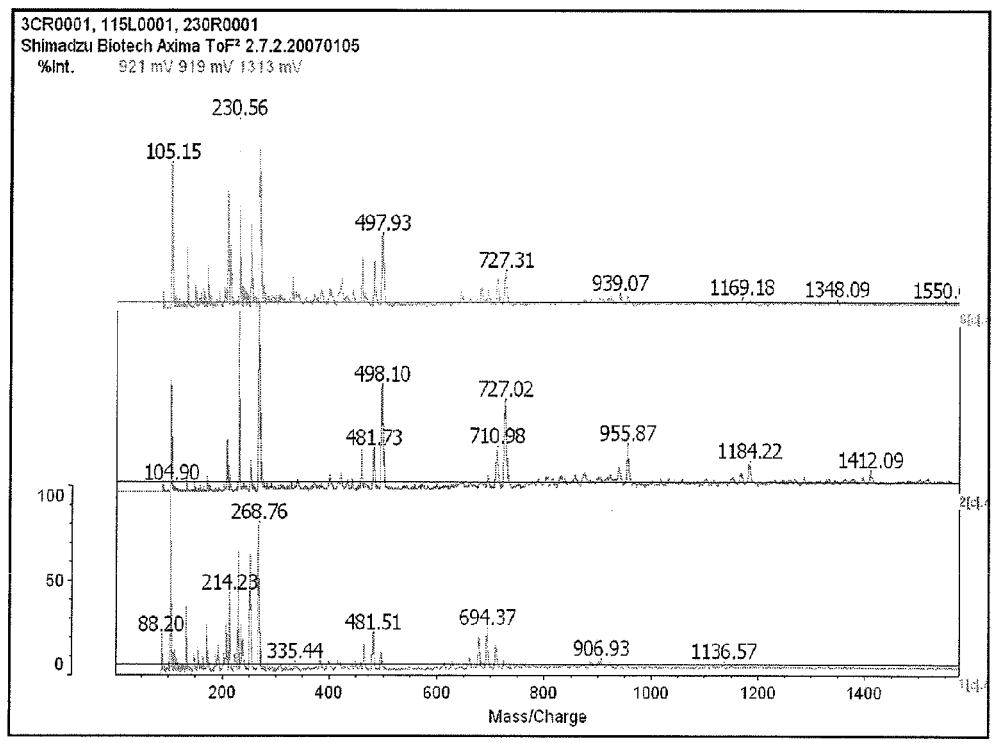

FIG. 4 represents MALDI, reflectron mode, control, bottom; 15 minutes post 3 Gy, center; and 30 minute post 3 Gy, top. Note 955.87 Da and 1184.12 Da peptides that appear at 15 minutes post 3 Gy, and the 939.07 Da peptide that appears 30 minute post 3 Gy.

Figure 5:
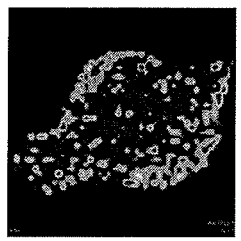

FIG. 5 represents a MALDI image of murine tongue one hour post 1 Gy TBI, longitudinal section. Note peripheral foci of Albumin (Red in image).

Figure 6:
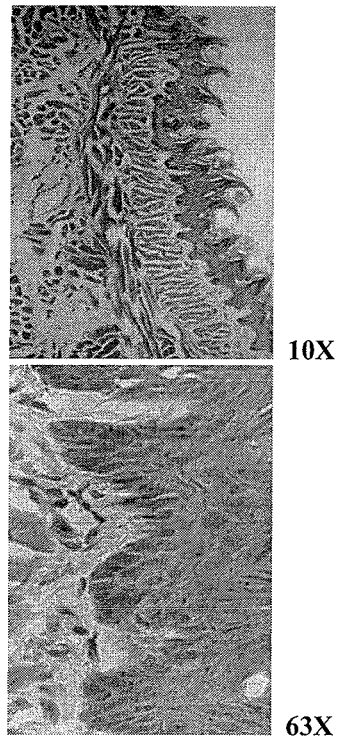

FIG. 6 depicts the histopathology of murine tongue one hour post 1 Gy TBI, longitudinal section. Note minimal destructive changes in the epithelial cornified spicule layer and edema in the basal region.

Figure 7:
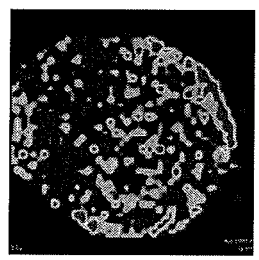

FIG. 7 represents a MALDI image. Note the marked increase in peripheral foci of Albumin compared to the post 1 Gy TBI image (Red in image).

Figure 8:
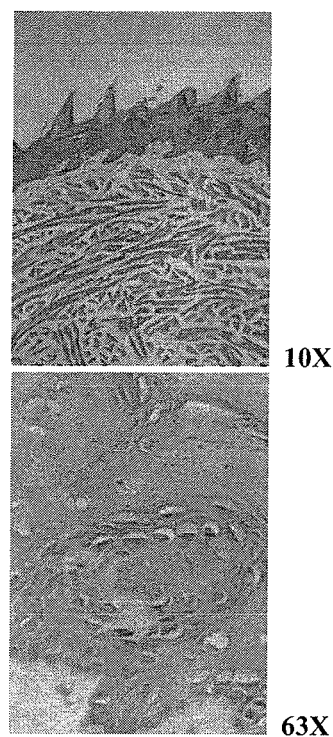

FIG. 8 depicts the histopathology of murine tongue one hour post 2 Gy TBI, longitudinal section. Note progressive destructive changes in the epithelial layer with disruption of the cornified spicule layer, increased scattered chromatin debris and edema of the sub-basement membrane layer.

Figure 9:
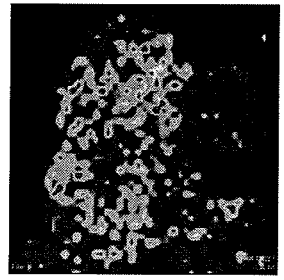

FIG. 9 represents a MALDI image of murine tongue one hour post 3 Gy TBI, longitudinal section. Note loss of peripheral foci of albumin consistant with destructive changes in the epithelial layer and increase in central foci of Albumin compared to the post 2 Gy image.

Figure 10:
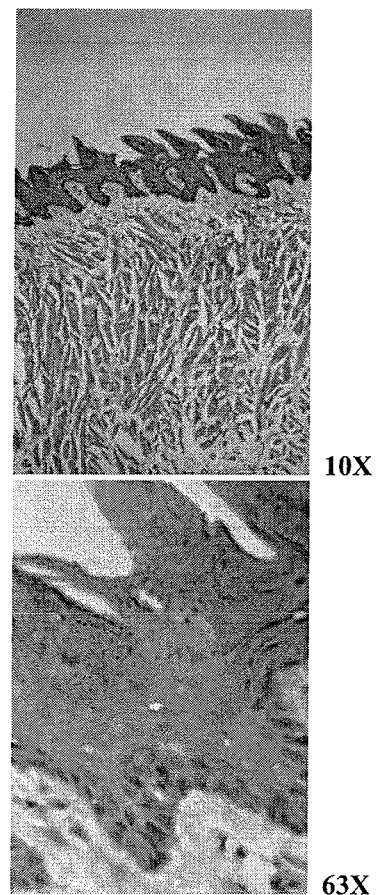

FIG. 10 depicts the histopathology of murine tongue one hour post 3 Gy TBI, longitudinal section. Note progressive destructive changes and virtual complete loss of the cornified spicule layer corresponding to the loss of peripheral albumin foci (peripheral zone) in the MALDI image, increased scattered chromatin debris, and increased edema of the sub-basement membrane layer.

Figure 11:

FIG. 11 represents the LAP monomer, light blue in the image.

Figure 12:
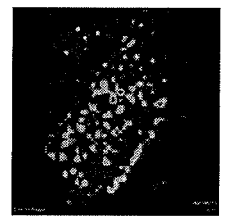

FIG. 12 represents the LAP monomer, light blue and red in the image.

Figure 13:
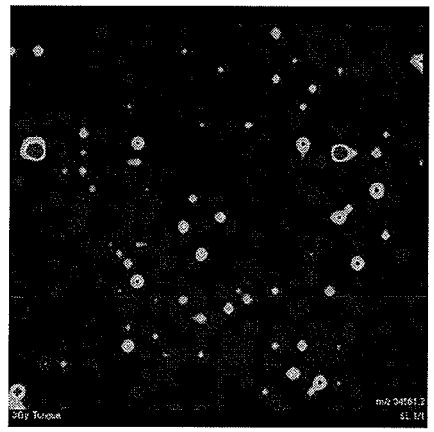

FIG. 13 represents the LAP monomer, light blue and red in the image.

Figure 14:
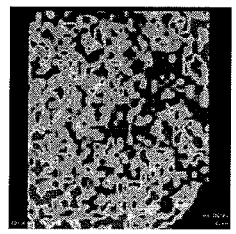
Figure 14:

FIG. 14 represents the Da Hemoglobin Subunit a, and Parathymosinare only found one hour post 1 Gy IR, red in the image.

Figure 15:
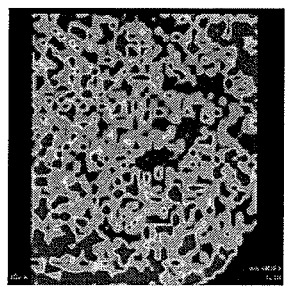
Figure 15:
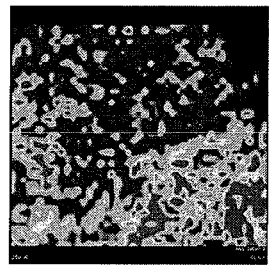

FIG. 15 depicts a fatty acid-binding protein adipocyte seen 1 hour post 1 and 2 Gy IR, red in the image.

Figure 16:
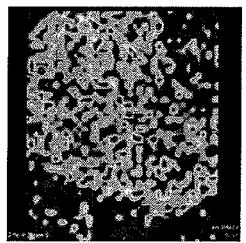
Figure 16:
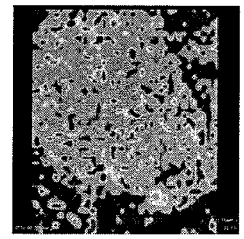

FIG. 16 demonstrates one hour post 2 Gy. Triosphosphate isomerase and superoxide dismutase are seen one hour post 2 Gy, but not seen in normal tissue or at one hour post 1 Gy. Red in the image.

Figure 17:
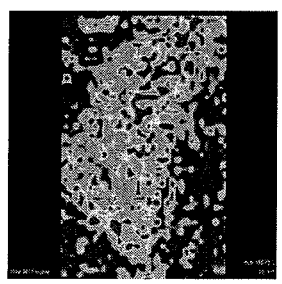
Figure 17:
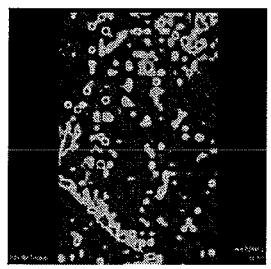

FIG. 17 demonstrates hemaglobin α chains and BC011074 NID seen one hour post 3 Gy.

DETAILED DESCRIPTION OF THE INVENTION

As used herein, the following terms mean as follows:

As used herein, "radiation associated marker" means any molecule, such as a protein, peptide or fragment thereof whose presence, absence or amount in absolute quantity or in quantity relative to other molecules may be used as evidence of exposure to elevated levels of ionizing radiation. Stated differently, a radiation associated marker may be any molecule that may be used as a statistically significant predictor of exposure to elevated levels of ionizing radiation, or that may used as a statistically significant predictor of the amount of ionizing radiation to which an individual has been exposed, or that may be used as a statistically significant predictor or clinical outcome post exposure to elevated levels of ionizing radiation.

As used herein, a "predetermined value" is a standardized value based on a control. For example, a predetermined value can be based on an amount of radiation associated marker that is present in a biological sample obtained from an individual.

The term "amount" is used within the context of the analytical method used to measure the different radiation associated markers and may reflect a number, a concentration, etc., depending upon the analytical method chosen to measure the radiation associated markers.

The term "biological sample," as used herein, generally refers to urine, saliva, serum, plasma, tears, or amniotic fluid. Buccal mucosa is an especially useful "biological sample" for the present invention because of its known sensitivity to ionizing radiation and easy accessibility for study.

The term "detecting" as used herein refers to identifying the presence of, identifying the presence of in relative amounts relative to another molecule or radiation associated marker relative to a predetermined value, or quantifying in absolute amounts.

The term "assessing exposure to ionizing radiation" includes quantifying the amount of ionizing radiation to which an individual has been exposed, quantifying the length of time to which an individual has been exposed to ionizing radiation, estimating or quantifying the amount of damage to a tissue or to an individual after exposure to ionizing radiation, and providing a prognosis of likely clinical sequelae or survival probability.

The term "elevated levels of ionizing radiation" encompasses instances where the ionizing radiation is present in amounts that are 10%, 20%, 30%, 50%, 75% or more greater than the amount of ionizing radiation experienced normally from environmental sources. The term "elevated levels of ionizing radiation" also encompasses instances where the ionizing radiation is present in amounts that are 2×, 3×, 4×, 5×, 10×, 25×, 50×, 100×, 500×, 1,000×, 5,000×, 10,000× 100,000×, 1,000,000× or more greater than the amount of ionizing radiation experienced normally from environmental sources. Ionizing radiation may be quantified and expressed in terms of a gray (Gy). One gray is the absorption of one joule of energy, in the form of ionizing radiation, by one kilogram of matter. For X-rays and gamma rays, these are the same units as the sievert (Sv). To avoid any risk of confusion between the absorbed dose and the equivalent dose, one must use the corresponding special units, namely the gray instead of the joule per kilogram for absorbed dose and the sievert instead of the joule per kilogram for the dose equivalent. The gray measures the deposited energy of radiation. The biological effects vary by the type and energy of the radiation and the organism and tissues involved. The sievert attempts to account for these variations. A whole-body exposure to 5 or more grays of high-energy radiation at one time usually leads to death within 14 days. This dosage represents 375 joules for a 75 kg adult (equivalent to the chemical energy in 20 mg of sugar). Since grays are such large amounts of radiation, medical use of radiation is typically measured in milligrays (mGy). The average radiation dose from an abdominal x-ray is 1.4 mGy, that from an abdominal CT scan is 8.0 mGy, that from a pelvic CT scan is 25 mGy, and that from a selective spiral CT scan of the abdomen and the pelvis is 30 mGy. One gray is equivalent to 100 rad. Therefore, the term "elevated levels of ionizing radiation" may be defined in some instances to mean a radiation dose greater than 0.25, 0.50, 1.0, 1.5, 2.0, 5.0, 10.0, 20.0, 50.0 or 100 mGy. In other instances, the term "elevated levels of ionizing radiation" may be defined to mean a radiation dose greater than 0.25, 0.50, 1.0, 1.5, 2.0, or 5.0 Gy.

According to an embodiment of this invention, the sample may be a saliva sample or a buccal swab. The sample may be obtained, for instance, about 15 minutes, 30 minutes, 1 hour, 2 hours, 6 hours, 12 hours, 1 day, 2 days or a week after exposure to elevated levels of ionizing radiation. In a particular embodiment of this invention, the sample is a buccal swab.

In addition, the present invention provides a method for determining the amount of radiation associated marker of in a sample comprising: (a) contacting the sample with an antibody which specifically binds to a radiation associated marker under conditions permitting formation of a complex between the antibody and the radiation associated marker; and (b) determining the amount of complexes formed thereby determining the amount of radiation associated marker in the sample.

This invention is illustrated in the experimental details section which follows. These sections are set forth to aid in an understanding of the invention but are not intended to, and should not be construed to limit in any way the invention as set forth in the claims which follow thereafter.

Radiation associated markers can be directly measured, for example, using anti-marker antibodies in an immunoassay, such as a Western blot or ELISA. Radiation associated markers can be indirectly measured, for example, using a capture antibody that binds the radiation associated marker.

The amount of radiation associated markers in a biological sample can be determined using any method known in the art, including, but not limited to, immunoassays using antibodies specific for the radiation associated marker. Any assay that functions to qualitatively or quantitatively determine variations in sample concentrations of radiation associated markers from normal levels can be employed in the practice of the invention.

For example, a monoclonal anti-radiation associated marker antibody can be generated by immunizing a mouse with the radiation associated marker. Once an immune response is detected, e.g., antibodies specific for the radiation associated marker are detected in the mouse serum, the mouse spleen is harvested and splenocytes are isolated. The splenocytes are then fused by well-known techniques to any suitable myeloma cells, for example, cells from cell line SP20 available from the American Type Culture Collection (ATCC). Hybridomas are selected and cloned by limited dilution. The hybridoma clones are then assayed by methods known in the art for cells that secrete antibodies capable of binding the radiation associated marker. Ascites fluid, which generally contains high levels of antibodies, can be generated by immunizing mice with positive hybridoma clones.

Any type of fusion phage, monoclonal, or polyclonal antibodies can be used in immunoassays of the invention, so long as the antibodies can be used in a reproducible fashion as markers for various radiation associated markers or as measures of the different levels of radiation associated markers observed in normal and variant populations.

In one embodiment, an amount of radiation associated marker can be measured using a capture antibody followed by a labeled secondary antibody using a strategy as described; for example, in U.S. Pat. No. 6,429,018, hereby incorporated by reference. The label on the secondary antibody can comprise any chemical, radioactive, lanthanide, colored dye, or genetic tag used in enzyme-linked immunosorbent assays (ELISAs), Western blots, and other sensitive and specific immunoassays and immunoradiometric assays using known methodology. These include conjugating the antibody with horseradish peroxidase or alkaline phosphatase that are easily measurable, typically using colorimetric, fluorometric or luminescent substrates. Genetic labels include firefly luciferase, employed because luciferase produces a bioluminescent molecule when incubated with its substrate, luciferin.

Figure 1:
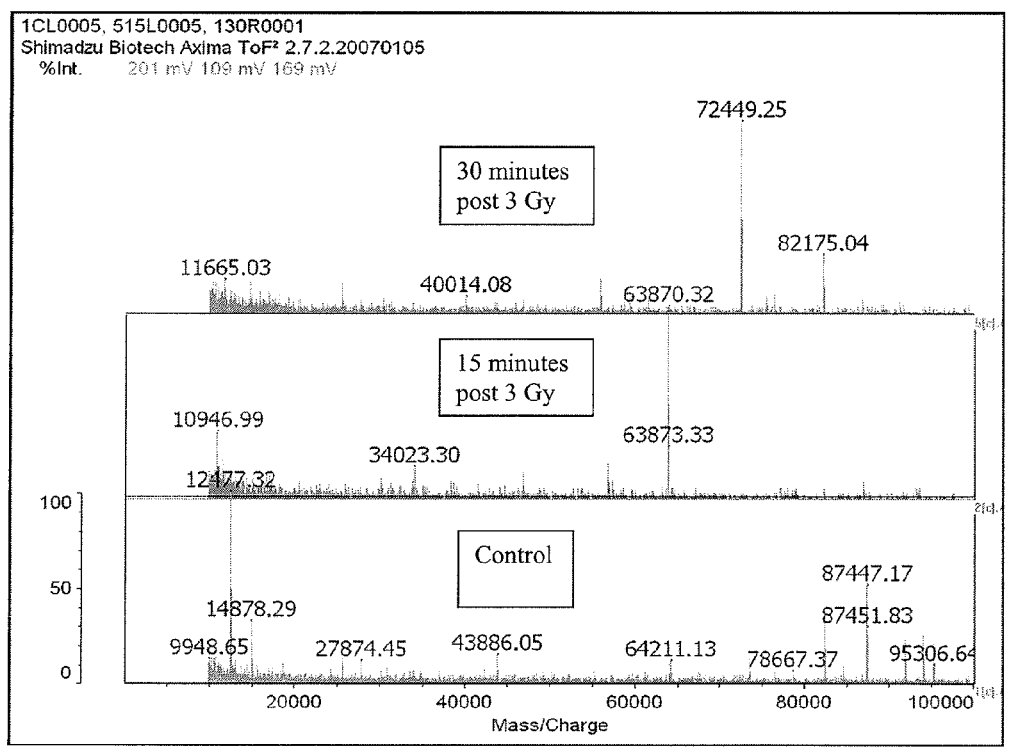
FIG. 1 demonstrates the presence of radiation associated biomarkers post exposure to elevated levels of ionizing radiation.
Figure 2:
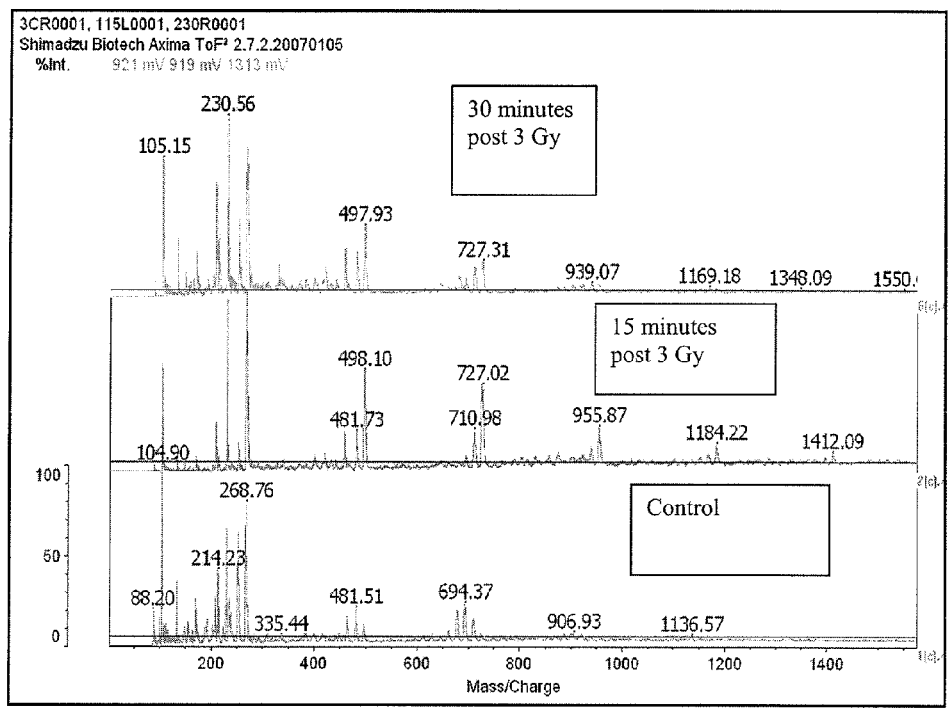
FIG. 2 demonstrates the presence of radiation associated biomarkers post exposure to elevated levels of ionizing radiation.

Serum albumin, by test strip, and numerous other novel protein and peptide biomarkers of ionizing radiation (IR) are consistently found by mass spectrometry in ex vivo wiping and histology sections of murine tongue epithelium one hour post 1, 2, and 3 Gy. Albumin and other proteins are not seen in non-irradiated tissue. Keratin is a ubiquitous component of tongue tissue, and can be seen at all levels of IR. The additional proteins in nonirradiated tissue, 1, 2, and 3 Gy are shown in the LCMS mass spectrometry Mascot search engine results. These biomarkers can be identified at POC with a simple oral cavity swab. FIG. 1. These biomarkers can be confirmed hours to days after the event with the same mass spectrometry techniques used in the initial biomarker identification with similar samples.

Matrix-Assisted Laser Desorption/Ionization (MALDI).

Matrix-assisted laser desorption/ionization (MALDI) is a soft ionization technique used in mass spectrometry, allowing the analysis of biomolecules (biopolymers such as proteins, peptides and sugars) and large organic molecules (such as polymers, dendrimers and other macromolecules), which tend to be fragile and fragment when ionized by more conventional ionization methods. It is most similar in character to electrospray ionization both in relative softness and the ions produced (although it causes many fewer multiply charged ions). The ionization is triggered by a laser beam (normally a nitrogen laser). A matrix is used to protect the biomolecule from being destroyed by direct laser beam and to facilitate vaporization and ionization.

The matrix consists of crystallized molecules, of which the three most commonly used are 3,5-dimethoxy-4-hydroxycinnamic acid (sinapinic acid), α-cyano-4-hydroxycinnamic acid (alpha-cyano or alpha-matrix) and 2,5-dihydroxybenzoic acid (DHB). A solution of one of these molecules is made, often in a mixture of highly purified water and an organic solvent (normally acetonitrile (ACN) or ethanol). Trifluoroacetic acid (TFA) may also be added. A good example of a matrix-solution would be 20 mg/mL sinapinic acid in ACN:water:TFA (50:50:0.1). The identity of suitable matrix compounds is determined to some extent by trial and error, but they are based on some specific molecular design considerations: they have a low molecular weight; they are acidic and act as a proton source to encourage ionization of the analyte; they have a strong optical absorption in the UV and efficiently absorb the laser irradiation; and they are functionalized with polar groups allowing use in aqueous solutions.

The matrix solution is mixed with the analyte (e.g. protein sample). The organic solvent allows hydrophobic molecules to dissolve into the solution, while the water allows for water-soluble (hydrophilic) molecules to do the same. This solution is spotted onto a MALDI plate (usually a metal plate designed for this purpose). The solvents vaporize, leaving only the recrystallized matrix, but now with analyte molecules spread throughout the crystals. The matrix and the analyte are said to be co-crystallized in a MALDI spot.

The laser is fired at the crystals in the MALDI spot. The matrix absorbs the laser energy, and the matrix is ionized by this event. The matrix transfers part of its charge to the analyte molecules (e.g. protein) thereby ionizing them while still protecting them from the disruptive energy of the laser. Ions observed after this process consist of a neutral molecule [M] and an added or removed ion. Together, they form a quasi-molecular ion, for example $[M+H]^+$ in the case of an added proton, $[M+Na]^+$ in the case of an added sodium ion, or $[M-H]^-$ in the case of a removed proton. MALDI is capable of creating singly-charged ions, but multiply charged ions $([M+nH]^{n+})$ can also be created, as a function of the matrix, the laser intensity and/or the voltage used. Note that these are all even-electron species. Ion signals of radical cations can be observed eg. in case of matrix molecules and other stable molecules.

Atmospheric pressure (AP) matrix-assisted laser desorption/ionization (MALDI) is an ionization technique (ion source) that in contrast to vacuum MALDI operates at normal atmospheric environment. In vacuum MALDI, ions are typically produced at 10 mTorr or less while in AP-MALDI ions are formed in atmospheric pressure.

AP-MALDI is used in mass spectrometry (MS) in a variety of applications including proteomics and drug discovery fields. AP-MALDI mass spectrometry is often used in proteomics, DNA/RNA/PNA, lipids, oligosaccharides, phosphopeptides, bacteria, small molecules and synthetic polymers, similar applications as available also for vacuum MALDI instruments.

The AP-MALDI ion source is easily coupled to an ion trap mass spectrometer or any other MS system equipped with ESI (electrospray ionization) or nanoESI source.

The type of a mass spectrometer most widely used with MALDI is the TOF (time-of-flight mass spectrometer) because of its large mass range. The TOF measurement procedure is suited to the MALDI ionization process since the pulsed laser takes individual 'shots' rather than working in continuous operation. MALDI-TOF instruments are typically equipped with an "ion mirror," deflecting ions with an electric field thereby doubling the ion flight path and increasing the resolution. Today, commercial reflectron TOF instruments reach a resolving power $m/\Delta m$ of well above 20'000 FWHM (full-width half-maximum, $\Delta m$ defined as the peak width at 50% of peak height).

In proteomics, MALDI is used for identifying proteins isolated through gel electrophoresis: SDS-PAGE, size exclusion chromatography, and two-dimensional gel electrophoresis. One method used is peptide mass fingerprinting by MALDI-MS, or with post ionization decay or collision-induced dissociation.

IMS.

The history of IMS (Imaging Maldi Spectroscopy) began with single cell studies of *Aplysia californica* neurons by matrix-assisted laser desorption/ionization time-of flight mass spectrometry (MALDI/TOF-MS). This was probably the first direct tissue MALDI identification of peptides and tissue profiling based on ion density. (Garden et al., *J Mass Spectrom* 1996; 31:1126-30) A refinement of this technique, imaging MALDI was described in human buccal mucosa, and rat pituitary and pancreas glands using two different approaches: direct targeting of the tissue itself and by analysis of blotted targets previously exposed to the tissue. (Caprioli et al., *Anal Chem* 1997; 69:4751-60) An "MS Image Tool," using the peptide neurotensin (peak at m/z 1674) significantly improved the data acquisition, speed of IMS, and utilization of the technique. (Stoeckli et al., *J Am Soc Mass Spectrom* 1999; 10:67-71) In a laser, capture microdissection (LCM) study of both tumor and normal human breast tissue fixed in ethyl alcohol, and stained with hematoxylin and eosin, normal tissue, carcinoma in situ, invasive carcinoma, and metastatic carcinoma could be distinguished by their different MALDI spectra. The introduction of "BioMap" software, by applying a baseline correction to the spectra and integrating over the peak of interest, demonstrated mouse brain images of amyloid 13, and A13 peptides. That report was proof of the principle that MALDI images of tissue could be obtained based upon the mass spectrometry mass/charge, m/z peak of interest. (Stoeckli et al., *Nat Med* 2001; 7:493-6) Subsequent profiling and IMS of normal mouse epididymis identified different protein activity (ion densities) throughout the sections. (Chaurand et al., *Electrophoresis* 2002; 23:3125-35)

The negative effects on IMS resolution from destructive tissue freezing artifacts, excessive dehydration due to ethanol fixation, paraformaldeyde cationization, embedding artifacts from OCT polymer and agar, and coarse matrix crystal size were first described in a report on spatial profiling of invertebrate ganglia. (Kruse et al., *J Am Soc Mass Spectrom* 2003; 14:752-9) In a follow-up report, they suggested a solution to the problem of freezing artifacts using glycerol and the related compounds ethane-1,2-diol and propane-1,2-diol to stabilize cellular membranes. (Rubakhin et al., *Anal Chem* 2003; 75:5374-80) A subsequent report suggested direct liquid nitrogen immersion of tissue in aluminum wrapping as a means of rapid fixation, but ignored the known consequences of freezer artifact. (Schwartz et al., *J Mass Spectrom* 2003; 38:699-708) Adjunctive histologic staining with methylene blue stained tissues on standard metal plates or indium-tin coated glass slides were shown to be compatible with IMS, but cresyl violet stain decreased IMS signal intensity. (Chaurand et al., *Anal Chem* 2004; 76:1145-55)

Tissue blotting with trypsin digestion for MSMS (mass spectrometry mass spectrometry using two mass spectrometers in tandem) data base analysis was shown to be useful in analyte localization, but was destructive to tissue morphology. (Bunch et al., *Rapid Communications in Mass Spectrometry* 2004; 18:3051-60) Others described a less destructive trypsin digest step to their prior tissue blotting technique for IMS. (Rohner et al., *Mech Ageing Dev* 2005; 126:177-85) Another method, matrix-enhanced secondary ion mass spectrometry (ME) SIMS was described and used for direct molecular imaging of the ganglia of the freshwater snail, *Lymnaea stagnalis*. (Altelaar et al., *Anal Chem* 2005; 77:735-41) However, this technique presented significant limitations and was proved unsuitable for direct tissue imaging. A refinement of IMS, oversampling with complete sample ablation at each sample position on the target plate, provided significant resolution enhancement with a translation stage raster step size of 25 μM. A 40 μM object could now be resolved with a 100 μM laser. (Jurchen et al., *Journal of the American Society for Mass Spectrometry* 2005; 16:1654-9)

Tissue treatments with organic solvents such as chloroform, acetone, hexane, toluene, or xylene were shown to be an effective and rapid method for signal enhancement in MALDI direct tissue profiling. (Lemaire et al., *Analytical Chemistry* 2006; 78:7145-53) These studies demonstrated that solvent treatments partially removed lipids from the tissue surface. Compared to previous studies with ethanol, chloroform/xylene solvent, rinsing is more specific for lipid removal and does not generate delocalization or extraction of most soluble peptides/proteins as tested by immuno-histochemistry experiments. Among all the tested solvents, chloroform and xylene produced the greatest increase in MALDI signal intensity and number of detected peptides/proteins. However, this treatment does not reduce salt adducts as does alcohol treatment. The results suggest that it is possible to detect, after organic rinsing treatments, compounds, such as peptides/proteins present in the cytoplasm, that were masked by lipids in the tissue.

Clench et al. reported the development and application of a method using 9-aminoacridine as a matrix for negatively charged ions in MALDI imaging. (Burrell et al., *J Exp Bot* 2007; 58:757-63) Crossman demonstrated the need for thin sections to avoid differential extraction efficiency of matrix solvent in different tissues. (Crossman et al., *Rapid Communications in Mass Spectrometry* 2006; 20:284-90) Pevsner demonstrated direct cellular MALDI identification of proteins in fixed cells and tissues without freezer artifact, tissue corrosion by matrix solvents or the use of tissue blotting. This was confirmed in a later report. (Pevsner et al., *Direct identification of proteins from cells and tissues using MALDI TOF. Anal Chem.*; Pevsner et al., *J Soc Gynecol Investig* 2006; 13:A1-B10; Groseclose et al., *J Mass Spectrom* 2007; 42:254-62)

Metal-assisted (MetA) secondary ion mass spectrometry (SIMS), a variation on SIMS as well as matrix-assisted laser desorption/ionization (MALDI) IMS can provide images from tissue, but the duration of these protocols were highly dependent on sample size and technique parameters. The duration of these studies averaged approximately 5 h. (Altelaar et al., *Nat Protoc* 2007; 2:1185-96)

Agar et al. studied multiple solvent/matrix combinations. However, the tissue sections at the electron microscopic level demonstrated both freezing artifact and structural distortion, indicating that their method disrupts normal subcellular structures such as mitochondria. (Agar et al., *Matrix Solution Fixation: Histology-Compatible Tissue Preparation for MALDI Mass Spectrometry Imaging. Anal Chem* 2007;.) Baluya et al reported a variation on inkjet-printed matrix application to tissue specimens previously described by Sloane et al. (Baluya et al., *Anal Chem* 2007; 79:6862-7; Sloane et al., *Mol Cell Proteomics* 2002; 1:490-9) The matrix application was of better quality and more reproducible than from specimens prepared by the electrospray and airbrush methods, but still was not completely uniform. A uniform method of tissue matrix application is sublimation. Sublimation is solvent free, rapid, and was successfully used to identify lipids in brain tissue, and more recently described for proteins or peptides. The challenge of IMS in formalin fixed paraffin embedded tissue was first addressed by and then by Pevsner and later by Stauber. (Hankin et al., *J Am Soc Mass Spectrom* 2007; 18:1646-52; Pevsner et al. "Microtubule Associated Proteins (MAP) and Motor Molecules: Direct Tissue MALDI Identification and Imaging." 2007; Pevsner et al., "Colon Cancer: Protein Biomarkers in Tissue and Body." 2007; Pevsner et al., "Colorectal Carcinoma—Field Defects in SatelliteTissue." 2007; Puolitaival et al., *J Am Soc Mass Spectrom* 2008; 19:882-6; Lemaire et al., *J Proteome Res* 2007; 6:1295-305; 48. Stauber et al., *J Proteome Res* 2008; 7:969-78)

This invention is illustrated in the experimental section that follows. These examples are set forth to aid in understanding the invention but are not intended to, and should not be construed to, limit in any way the invention as set forth in the claims.

EXAMPLE 1

New protein biomarkers were identified in murine buccal mucosa after ionizing radiation. The new protein biomarkers were identified from scraping of buccal mucosa obtained fifteen and thirty minutes post ionizing radiation exposure. The biomarkers are as follows:

DnaJ homolog subfamily C member 1 (DnaJ protein homolog MTJ1) gi|2494160|sp|Q61712.1|DNJC1_MOUSE[2494160. DnaJ domain. DnaJ domains (J-domains) are associated with hsp70 heat-shock system and it is thought that this domain mediates the interaction which is triggered by ionizing radiation.

mCG1463, isoform CRA_b [*Mus musculus*] gi|148683958|gb|EDL15905.1|[14868395]. This protein is involved in transcriptional regulation which is triggered by ionizing radiation.

The following three proteins all represent biomarkers of acute radiation exposure which triggers either transcription or post-translational modification.

Novel protein (B230312A22Rik) [*Mus musculus*] 955.87 Da
Amino Acid Sequence: MSGPRKAPED
gi:45593111 Demonstrated 15 minutes post ionizing radiation.

Unnamed protein product [*Mus musculus*] 1184.12 Da
Amino Acid Sequence: AKDYYGTGYF
gi|1333908| Demonstrated 15 minutes post ionizing radiation.

Transaldolase [*Mus musculus*] 939.07 Da
Amino Acid Sequence: MRHVQAELS
gi|168984609| Demonstrated 30 minutes post ionizing radiation.

The identification of specific protein biomarker profiles and new protein biomarkers of ionizing radiation exposure enable reliable associations with dose-exposure, for biodosimetry purposes. This strategy will result in the development of diagnostic tests using a buccal mucosa swab to provide acute clinical quantitative evidence of radiation exposure of 3 Gy or more and allow for accurate and immediate triage of victims of an ionizing radiation mass casualty.

EXAMPLE 2

Fourteen swiss mice were anesthetized with intraperitoneal ketamine-xylazine (k/x, 80/10 mg/kg ip). Ten mice received 3 Gy to the head. Buccal mucosa scrapings were obtained fifteen minutes (5 mice) and thirty minutes (five mice) post exposure. Buccal mucosa scrapings from the four non-radiated mice were used as controls. All reagents were obtained from Sigma (St. Louis, Mo.) and used unmodified. All samples were placed in 1 mL of 100 mMolar ammonium bicarbonate buffer. Proteins were extracted from all the tissues in this buffer with high pressure (Barocycler, Pressure BioSciences, South Easton, Mass.). The samples were concentrated by lyophilization to 200 µL and divided into three components. One for trypsin digestion and liquid chromatography mass spectrometry, LCMS, analysis (bottoms-up proteomics), one for HPLC protein separation and FTMS analysis (top-down proteomics) to identify post-translational modifications (this aliquot was frozen for later analysis), and one for direct identification with matrix assisted laser desorption mass spectrometry, MALDI analysis. The study was conducted under an approved protocol of the New York University School of Medicine Institutional Animal Care and Use Committee, Laboratory Animal Protocol #080601-01.

Sinapic acid (5 mg/mL) 0.3 µL was pipetted onto a conductive MALDI plate, allowed to dry, and covered with an equal amount of sample. All fourteen samples were examined with MALDI in linear mode. The findings were consistent across all four controls, 15 minute (N=5), and 30 minute (N=5) samples, FIG. 3. Cyano 4 hydroxy cinnamic acid (5 mg/mL) 0.3 µL was pipetted onto a conductive MALDI plate, allowed to dry, and covered with an equal amount of sample. All fourteen samples were examined with MALDI in reflectron mode. The findings were consistent across all four controls, 15 minute (N=5), and 30 minute (N=5) samples, FIG. 4.

Results.

Figure 3:
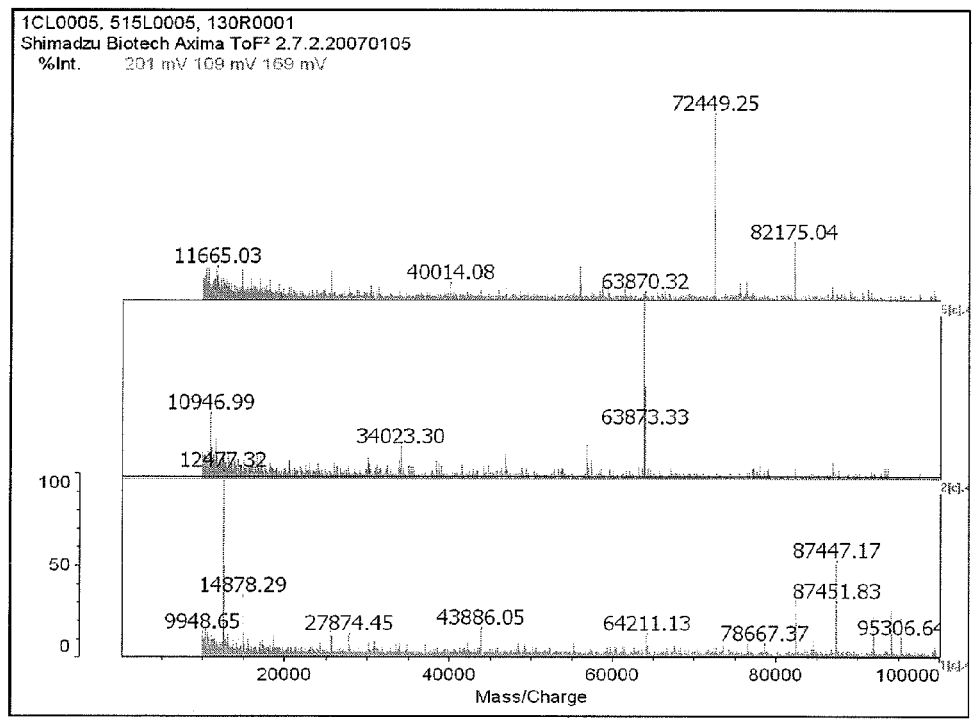
FIG. 3 represents a MALDI spectrum, linear mode, control, 15 minutes post 3 Gy, and 30 minute post 3 Gy. Note the protein peaks 63870.32 Da at 15 minutes, and 72449.25 at 30 minutes. These proteins can be tentatively identified with bioinformatics in the NCBInr database. The tip of the 63870.32 peak is superimposed on the bottom of the 30 minute spectrum.

The linear mode MALDI MS experiment is shown in FIG. 3. The lowest spectrum is a control sample. The middle spectrum is a 15 minute post 3 Gy sample. The upper spectrum is a 30 minute post 3 Gy sample. At 15 minutes post 3 Gy, a protein 63870.32 Da, D naJ homolog subfamily C member 1 (DnaJ protein homolog MTJ1) gi|2494160|sp|Q61712.1|DNJC1_MOUSE[2494160] was demonstrated. DnaJ domains (J-domains) are associated with hsp70 heat-shock system and it is thought that this domain mediates the interaction. At 30 minutes post 3 Gy, a protein 72449.25 Da, mCG 1463, isoform CRA_b [Mus musculus] gi|148683958|gb|EDL15905.1|[14868395] is tentatively identified in the spectrum. This protein is involved in transcriptional regulation. At 15 and 30 minutes post 3 Gy, the spectrum of peptides is demonstrated in FIG. 4, and the peptide amino acid sequences derived with bioinformatics and the corresponding proteins they represent are shown in Table 1.

These experiments demonstrated novel changes 15 and 30 minutes post ionizing radiation to the head and neck.

EXAMPLE 3

Additional experiments using total body ionizing radiation (N=21), TBI, exposure at 0 (N=3), 1 (N=6), 2 (N=6), and 3 (N=6) Gy were performed (mice). The murine tongue was chosen for examination. The mice were sacrificed at one hour post TBI, MALDI imaging of tongue tissue was combined with high resolution, 1.43 nm, (IR filter visible light 400 nm, Zeiss 63X oil immersion 1.4 NA objective, and 1.4 NA Olympus condenser) bright field microscopy (the smallest mitochondria are 1000 nm); and liquid chromatography mass spectrometry, LCMS, to obtain protein sequence data for exact identification and localization of post TBI protein biomarkers in the tissue sections. Protein extraction from the $3^{rd}$ contiguous section was performed with a Barocycler and digested with trypsin for LCMS examination. Contiguous 5µ cryo-sections were obtained for MALDI imaging, examples of normal, post 1, 2, and 3 Gy, FIGS. 5-10; histology (hematoxylin and eosin, H&E), examples of normal, post 1, 2, and 3 Gy, FIGS. 5-10; and nanoflow liquid chromatography mass spectrometry, LCMS, examples of normal, post 1, 2, and 3 Gy. The molecular weights of the identified proteins were used in the MALDI image prepared with sublimation for tissue localization. (Naftolin et al., Reproductive Sciences 2007; 14:257A; Pevsner et al., Biomarkers Med 2009; 3:55. FIG. 5 represents a MALDI image of murine tongue one hour post 1 Gy TBI, longitudinal section. Note peripheral foci of Albumin (Red in image). FIG. 6 demonstrates the histopathology of murine tongue one hour post 1 Gy TBI, longitudinal section. Note minimal destructive changes in the epithelial cornified spicule layer and edema in the basal region. FIG. 7 represents a MALDI image Note marked increase in peripheral foci of Albumin compared to the post 1 Gy TBI image (Red in image).

FIG. 8 demonstrates the histopathology of murine tongue one hour post 2 Gy TBI, longitudinal section. Note progressive destructive changes in the epithelial layer with disruption of the cornified spicule layer, increased scattered chromatin debris and edema of the sub-basement membrane layer. FIG. 9 represents a MALDI image of murine tongue one hour post 3 Gy TBI, longitudinal section. Note loss of peripheral foci of albumin consistant with destructive changes in the epithelial layer and increase in central foci of Albumin compared to the post 2 Gy image. FIG. 10 demonstrates the histopathology of murine tongue one hour post 3 Gy TBI, longitudinal section. Note progressive destructive changes and virtual complete loss of the cornified spicule layer corresponding to the loss of peripheral albumin foci (peripheral zone) in the MALDI image, increased scattered chromatin debris, and increased edema of the sub-basement membrane layer.

TABLE 1

Peptide amino acide sequence and corresponding proteins identified with bioinformatics at 15 and 30 minutes post 3 Gy.
Peptides at 15 and 30 min post 3 Gy

| | | | | |
|---|---|---|---|---|
| 15 min | 955.87 | gi|4559311| novel protein(B230312A22Rik) [Mus musculus] | msgprkaped | (SEQ ID NO: 1) |
| | 1184.12 | gi|1333908|unnamed protein product [Mus musculus] | akdyygtgyf | (SEQ ID NO: 2) |
| 30 min | 939.07 | gi|168984609|transaldolase [Mus musculus]. | mrhvqaels | (SEQ ID NO: 3) |

TABLE 2

{MATRIX SCIENCE} Mascot Search Results

| | |
|---|---|
| User: | NYUSOM |
| Email: | seagea01@nyumc.org |
| Search title: | |
| MS data file: | E:\20090324_LCMS_Samples\1_001_CID.mgf |
| Database: | MSDB 20060831 (3239079 sequences; 1079594700 residues) |
| Taxonomy: | *Mus musculus* (house mouse) (90914 sequences) |
| Timestamp: | Apr. 8, 2009 at 13:25:26 GMT |

Protein hits:

| | |
|---|---|
| AAH11074 | BC011074 NID: - *Mus musculus* |
| K1C17_MOUSE | Keratin, type I cytoskeletal 17 (Cytokeratin-17) (CK-17) (Keratin-17) (K17). - *Mus musculus* (Mouse). |
| Q2M1G8_MOUSE | 2410039E07Rik protein (Fragment). - *Mus musculus* (Mouse). |
| KRMSE1 | keratin, 59K type I cytoskeletal - mouse |
| K1C15_MOUSE | Keratin, type I cytoskeletal 15 (Cytokeratin-15) (CK-15) (Keratin-15) (K15). - *Mus musculus* (Mouse). |
| Q32P04_MOUSE | Krt2-5 protein (Fragment). - *Mus musculus* (Mouse). |
| Q8BGZ7_MOUSE | 10 days neonate skin cDNA, RIKEN full-length enriched library, clone: 4732475I03 product: CYTOKERATIN homolog (10 days neonate skin CDNA, RIKEN full-length enriched library, clone: 4732468K03 product: CYTOKERATIN TYPE II homolog) (6 days neonate skin cD |
| K2C6A_MOUSE | Keratin, type II cytoskeletal 6A (Cytokeratin-6A) (CK 6A) (K6a keratin) (Keratin-ϵ alpha) (mK6-alpha). - *Mus musculus* (Mouse). |
| A55682 | keratin 13, type I cytoskeletal - mouse |
| Q8K2E4_MOUSE | CDNA sequence BC031593. - *Mus musculus* (Mouse). |
| JQ0028 | cytokeratin 19 - mouse |
| Q9D2K8_MOUSE | 0 day neonate head cDNA, RIKEN full-length enriched library, clone: 4833436C19 product: keratin complex 2, basic, gene 1, full insert sequence. - *Mus musculus* (Mouse). |
| KRMS2 | keratin, type II cytoskeletal - mouse (fragment) |
| Q3TTY5_MOUSE | 10 days neonate skin cDNA, RIKEN full-length enriched library, clone: 4732404G19 product: keratin complex 2, basic, gene 17, full insert sequence (10 days neonate skin cDNA, RIKEN full-length enriched library, clone: 4732426A12 product: keratin complex |
| S07330 | keratin, epidermal - mouse |
| A26135 | keratin, 52K type I epidermal (clone pke 52) - mouse (fragment) |
| Q80VP7_MOUSE | Hypothetical protein MGC54654. - *Mus musculus* (Mouse). |
| Q6IFT3_MOUSE | Keratin Kb40. - *Mus musculus* (Mouse). |
| Q8BIS2_MOUSE | 10 days neonate skin cDNA, RIKEN full-length enriched library, clone: 4732456N10 product: similar to KERATIN, TYPE II CYTOSKELETAL 6D (CYTOKERATIN 6D) (CK 6D) (K6D KERATIN). - *Mus musculus* (Mouse). |
| Q6NXH9_MOUSE | Type II keratin Kb36. - *Mus musculus* (Mouse). |
| K2C1B_MOUSE | Keratin, type II cytoskeletal 1b (Type II keratin Kb39) (Embryonic type II keratin-1). - *Mus musculus* (Mouse). |
| BAE40567 | AK168726 NID: - *Mus musculus* |
| K2C4_MOUSE | Keratin, type II cytoskeletal 4 (Cytokeratin-4) (CK-4) (Keratin-4) (K4) (Cytoskeletal 57 kDa keratin). - *Mus musculus* (Mouse). |
| Q3UV17_MOUSE | Adult female vagina cDNA, RIKEN full-length enriched library, clone: 9930024P18 product: similar to Keratin 2p. - *Mus musculus* (Mouse). |
| I59009 | epidermal keratin subunit II - mouse |
| Q9Z1R9_MOUSE | Trypsinogen 16 (Protease, serine, 1). - *Mus musculus* (Mouse). |
| Q9CXH5_MOUSE | 17 days embryo head cDNA, RIKEN full-length enriched library, clone: 3300001P16 product: hemoglobin, beta adult major chain, full insert sequence. - *Mus musculus* (Mouse). |
| Q6IME9_MOUSE | Type-II keratin Kb35. - *Mus musculus* (Mouse). |
| Q9JJ20_MOUSE | 14-3-3 protein sigma - *Mus musculus* (Mouse). |
| H2B1B_MOUSE | Histone H2B type 1-B (h2B-143). - *Mus musculus* (Mouse). |
| Q8BKC6_MOUSE | 0 day neonate eyeball cDNA, RIKEN full-length enriched library, clone: E130120J09 product: hypothetical Intermediate filament proteins containing protein, full insert sequence. (Fragment). - *Mus musculus* (Mouse). |
| I48739 | MHa2 (keratin acidic 2) - mouse |
| H2A2A_MOUSE | Histone H2A type 2-A (H2A.2). - *Homo sapiens* (Human). |
| HAMS | hemoglobin alpha chains - mouse |
| BAC33789 | AK049517 NID: - *Mus musculus* |

Probability Based Mowse Score

Ions score is −10 * Log (P), where P is the probability that the observed match is a random event.

Individual ions scores > 38 indicate identity or extensive homology (p < 0.05).

Protein scores are derived from ions scores as a non-probabilistic basis for ranking protein hits.

Table 2 provides the results of a Mascot search of proteins in normal murine tongue. No albumin was identified.

TABLE 3

Peptide Summary Report(../data/20090408/FtiAifuwe.dat)
{MATRIX SCIENCE} Mascot Search Results

| | |
|---|---|
| User | NYUSOM |
| Email | seagea01@nyumc.org |
| Search title | |
| MS data file | E:\20090324_LCMS_Samples\9_001_CID.mgf |
| Database | MSDB 20060831 (3239079 sequences; 1079594700 residues) |
| Taxonomy | Mus musculus (house mouse) (90914 sequences) |
| Timestamp | 8 Apr. 2009 at 13:57:09 GMT |
| Protein hits | Q8BGZ7_MOUSE — 10 days neonate skin cDNA, RIKEN full-length enriched library, clone: 4732475I03 product:CYTOKERATIN homolog (10 days neonate skin cDNA, RIKEN full-length enriched library, clone: 4732468K03 product: CYTOKERATIN TYPE (1 homolog) (6 days neonate skin cD |
| | K2C1-MOUSE — Keratin, type I: cytoskeletal 1 (Cytokeratin-1) (CK-1) (Keratin-1) (K1) (67 kDa cytokeratin).- Mus musculus (Mouse). |
| | Q9D2K8_MOUSE — 0 day neonate head cDNA, RIKEN full-length enriched library, clone: 4833436C19 product: keratin complex 2, basic, gene 1, full insert sequence.- Mus musculus (Mouse). |
| | Q32P04_MOUSE — Krt2-5 protein (Fragment).- Mus musculus (Mouse). |
| | K2C6A_MOUSE — Keratin, type II cytoskeletal 6A (Cytokeratin-6A; (CV 6A) (K6a keratin) (Keratin-6 alpha) (mk6-alpha).- Mus musculus (Mouse). |
| | Q80VPP7_MOUSE — Hypothetical protein MGC54654.- Mus musculus (Mouse). |
| | Q8BIS2_MOUSE — 10 days neonate skin cDNA, RIVEN full-length enriched library, clone: 4732456N10 product: similar to KERATIN, TYPE II CYTOSKELETAL 6D (CYTOKERATIN 6D) (CK CD) (K6D KERATIN).- Mus musculus (Mouse). |
| | Q9CXH5_MOUSE — 17 days embryo head cDNA, RIKEN full-length enriched library, clone: 3300001P16 product: hemoglobin, beta adult major chain, full insert sequence.- Mus musculus (Mouse) |
| | KRMSE1 — keratin, 59K type I cytoskeletal - mouse |
| | Q6NXH9_MOUSE — Type II keratin in Kb36.- Mus musculus (Mouse). |
| | K2C1B_MOUSE — Keratin, type II cytoskeletal lb (Type II keratin Kb39) (Embryonic type II keratin-1).- Mus musculus (Mouse). |
| | Q6IFZ9_MOUSE — TYPE II keratin Kb37.- Mus musculus (Mouse). 10 days neonate skin cDNA, RIKEN full-length enriched library, clone: 4732404G19 product: keratin complex 2, basic, gene 17, full insert sequence (10 days neonate skin cDNA, RIKEN full-length enriched library, clone: 4732426A12 product: keretin complex |
| | Q6IFT3_MOUSE — Keratin, Kb40.- Mus musculus (Mouse). |
| | Q3UV17_MOUSE — Adult female vagina cDNA, RIKEN full-length enriched library, clone: 9930021P18 product:similar to Keratin 2p.- Mus musculus (Mouse). |

Table 3 lists LCMS identified proteins with Mascot search of proteins in murine tongue one hour post 1 Gy TBI. Albumin appears at the end of the list and corresponds to the findings in the MALDI image one hour post 1 Gy.

TABLE 4

Peptide Summary Report(../data/20090408/FtiAifsSE.dat)
{MATRIX SCIENCE} Mascot Search Results

| | |
|---|---|
| User | NYUSOM |
| Email | seagea01@nyumc.org |
| Search title | |
| MS data file | E:\20090324_LCMS_Samples\10_001_CID.mgf |
| Database | MSDB 20060831 (3239079 sequences; 1079594700 residues) |
| Taxonomy | Mus musculus (house mouse) (90914 sequences) |
| Timestamp | 8 Apr. 2009 at 14:03:15 GMT |
| Protein hits | KRMSE1 — keratin, 59K type I cytoskeletal - mouse |
| | Q9CY54_MOUSE — 13 days embryo liver cDNA, RIKEN full-length enriched library, clone: 2500004H04 product: hemoglobin, beta adult major chain, full insert sequence.- Mus musculus (Mouse). |
| | HAMS — hemoglobin alpha grains - mouse |
| | Q9CY06_MOUSE — 13 days embryo liver cDNA, RIKEN full-length enriched library, clone: 2510040P05 product: hemoglobin, beta adult major chain, full insert sequence.- Mus musculus (Mouse). |
| | AAH11074 — BC011074 NID: - Mus musculus |
| | HBMS — hemoglobin beta major chain - mouse |
| | Q3TTY5_MOUSE — 10 days neonate skin cDNA, RIKEN full-length enriched library, clone: 4732404G19 product:keratin complex 2, basic, gene 17, full insert sequence (10 days neonate skin cDNA, RIKEN full-length enriched library, clone: 4732426A12 product:keratin complex |
| | Q3UJH8_MOUSE — 16 days embryo heart cDNA, RIKEN full-length enriched library, clone: I32000IF12 product: glutamate oxaloacetate transarunaso 1, soluble, full insert sequence.- Mus musculus(Mouse) |
| | Q8BGZ7_MOUSE — 10 days nenoate skin cDNA, RIKEN full-length enriched library, clone: 4732475I03 product:CYTOKERATIN homolog (10 days neonate skin cDNA, RIKEN |

TABLE 4-continued

Peptide Summary Report(../data/20090408/FtiAifsSE.dat)
{MATRIX SCIENCE} Mascot Search Results

|  |  |
|---|---|
|  | full-length enriched library, clone: 4732468K03 product: CYTOKERATIN TYPE II homolog) (6 days neonate skin cD |
| K1C17_MOUSE | Keratin, type I cytoskeletal 17 (Cytokeratin-17) (CK-17) (Keratine-17) (K17).- Mus musculus (Mouse). |
| Q9R0S6_MOUSE | Beta-1-globin (Fragment).- Mus musculus (Mouse). |
| K2C1_MOUSE | Keratin, type II cytoskeletal 1 (Cytokeratin-1) (CK-1) (Keratin-1) (K1) (67 kDa) cytokeratin).- Mus musculus (Mouse). |
| Q9D2K8_MOUSE | 0 day neonate head cDNA, RIKEN full-length enriched library, clone: 4833436C19 product: keratin complex 2, basic, gene 1, full insert sequence.- Mus musculus (Mouse). |
| A55682 | keratin 13, type I cytoskeletal - mouse |

Table 4 lists LCMS identified proteins with Mascot search of proteins in murine tongue one hour post 2 Gy TBI. Albumin appears next to last in the list.

TABLE 5

Peptide Summary Report(../data/20090408/FtiAifsEL.dat)
{MATRIX SCIENCE} Mascot Search Results

| User | NYUSOM |  |
|---|---|---|
| Email | seagea01@nyumc.org |  |
| Search title |  |  |
| MS data file | E:\20090324_LCMS_Samples\16_001_CID.mgf |  |
| Database | MSDB 20060831 (3239079 sequences; 1079594700 residues) |  |
| Taxonomy | Mus musculus (house mouse) (90914 sequences) |  |
| Timestamp | 8 Apr. 2009 at 14:05:43 GMT |  |
| Protein hits | HAMS | hemoglobin alpha chains - mouse |
|  | Q9CY12_MOUSE | 13 days embryo liver cDNA, RIKEN full-length enriched library, clone: 2510039D09 product: hemoglobin, beta adult major chain, full insert sequence.- Mus musculus (Mouse). |
|  | Q8BGZ7_MOUSE | 10 days neonate skin cDNA, RIKEN full-length enriched library, clone: 4732475I03 product: CYTOKERATIN homolog (10 days neonate skin cDNA, RIKEN full length enriched library, clone: 4732468K03 product: CYTOKERATIN TYPE II homolog) (6 days neonate skin cD |
|  | Q32P04_MOUSE | Krt2-5 protein (Fragment).- Mus musculus (Mouse). |
|  | Q3TV03_MOUSE | Adult male stomach cDNA, RIKEN full-length enriched library, clone: 2210414C06 product:albumin 1, full insert sequence.- Mus musculus (Mouse). |
|  | KRMSE1 | keratin, 59K type I cytoskeletal - mouse |
|  | K1C15_MOUSE | Keratin, type I cytoskeletal 15 (Cytokeratin-15) (CK-15) (Keratin-15) (K15).- Mus musculus (Mouse). |
|  | Q8BIS2_MOUSE | 10 days nenoate skin cDNA, RIKEN full-length enriched library, clone: 4732456N10 product:smilar to KERATIN, TYPE II CYTOSKELETAL 6D (CYTOKERATIN 6D) (CK 6D) (KcD KERATIN).- Mus musculus (Mouse). |

Probability Based Mowse Score
Ions score is $-10 * \text{Log}(P)$, where P is the probability that the observed match is a random event.
Individual ions scores > 38 indicate identity or extensive homology (p < 0.05).
Protein scores are derived from ions scores as a non-probabilistic basis for ranking protein hits.

Table 5 lists LCMS identified proteins from two separate samples 16 and 19. Mascot search of proteins in murine tongue one hour post 3 Gy TBI. The absence of albumin in these two 3 Gy samples, it was present in other 3 Gy samples (data not shown) is consistent with the marked tissue destruction, and very small amount noted in the MALDI image.

EXAMPLE 4

It has been shown (MHB) that latent transforming growth factor-β, LTGF-β, is rapidly activated in vivo after ionizing radiation (IR). This is evidenced by increased immunoreactivity of TGFβ epitopes that are masked by the latent complex. (Barcellos-Hoff *Mol Biol Cell* 1994; 5:139a; Barcellos-Hoff et al., *Am J Pathol* 1995; 147:1228-37; Barcellos-Hoff et al., *Molec Endocrin* 1996; 10:1077-83; Barcellos-Hoff et al., *Mol Endocrinol* 1996; 10:1077-83; Barcellos-Hoff Mammary Gland *Biol Neoplasia* 1996; 1:353-63; Ehrhart et al., *FASEB J* 1997; 11:991-1002; Barcellos-Hoff et al., *Breast Cancer Res* 2000; 2:92-9; Barcellos-Hoff et al., *Nat Rev Cancer* 2005; 5:867-75; Jobling et al., *Radial Res* 2006; 166:839-48; Jobling et al., *Radial Res* 2006; 166:839-848). Because reactive oxygen species, ROS, are a product of the interaction of IR with water or with cell membranes, it was postulated that the rapid activation of TGFβ in vivo could be due to ROS generated by IR if the protein itself contained redox sensitive amino acids. We were able to demonstrate the monomers of TGFβ and the latency associated protein, LAP, in MALDI images one hour post 1, 2, and 3 Gy, FIGS. 18,19, 20. Note the approximately 10 Da variance in all three images. This molecular weight variance and spatial resolution can be improved, infra vida. Therefore TGFβ can also be used as a protein biomarker of absorbed dose. Quantization can be obtained from trypsin digests studied by LCMS. FIGS. 11, 12 and 13 depict LAP monomers, light blue in the image.

Additional dose specific protein biomarkers identified from other LCMS studies were not seen in normal tissue. Hemoglobin subunit α, and parathymosinare only found one hour post 1 Gy; Fatty Acid Binding Protein Adipocyte seen 1 hour post 1 and 2 Gy IR; and triosphosphate Isomerase, and superoxide dismutase seen at one hour post 2 Gy are not seen in normal tissue or at one hour post 1 Gy.

FIG. 14 depicts da hemoglobin subunit α, and parathymosinare only found one hour post 1 Gy IR, red in the image. FIG. 15 depicts fatty acid-binding protein adipocyte seen 1 hour post 1 and 2 Gy IR, red in the image. FIG. 16 depicts one hour post 2 Gy exposure. Triosphosphate isomerase and superoxide dismutase are seen one hour post 2 Gy, but not seen in normal tissue or at one hour post 1 Gy (red in the image). FIG. 17 demonstrates hemaglobin α chains and BC011074 NID seen one hour post 3 Gy exposure.

The results with MALDI imaging, high resolution microscopy, and LCMS are proof of principle that post TBI protein biomarkers can be identified and used as measures of absorbed radiation dose at 1, 2, and 3 Gy with our current technology. Identification of a larger library of post TBI proteins will improve specificity of both the POC triage kit and the HT device. This will dramatically limit false positives and false negatives. This will be achieved with a combination of strategies including higher resolution bright field microscopy, atomic force microscopy of irradiated tissue for higher spatial resolution of tissue loci of proteins by co-registration with the MALDESI images. (Collier et al., *Anal Chem* 2008; 80:4994-5001; Bereman et al., *Rapid Commun Mass Spectrom* 2008; 22:1563-6; Sampson et al., *J Am Soc Mass Spectrom* 2009; 20:667-73). Separation of extracted proteins is performed by 2D cation exchange LCMS with high-throughput electron capture dissociation (ECD) analysis to identify post translational modification of IR induced protein biomarkers; modifying sublimation matrix application by varying time, temperature and distance between the matrix powder platform and the mounted tissue, FIG. 16; thinner tissue sections with a high performance cryostat; and complete removal of tissue embedding media polymer residue by varying solvent baths.

The application of matrix assisted laser distortion electrospray ionization Fourier transform ion cyclotron mass spectrometry, FTICR, for both liquid samples and imaging, MALDESI imaging, will improve the isotopic resolution by 2 orders of magnitude. The MALDI system full width half mass, FWHM, isotopic resolution is 2500 Da. The MALDESI system full width half mass, FWHM, isotopic resolution is 250,000 Da. The spatial resolution of MALDI images will improve with laser $M^2$ beam quality closer to 1, increased repetition rate, Hz, fluence, mj/s (Watts), Energy, E, mj/pulse, pulse width, increased work function, smaller spot size, and, optics (beam focus); and decremental sample stage movement from microns to nanometers.

The following Table 6 provides examples of other potential biomarkers of ionizing radiation isolated from buccal tissue in subsequent examples obtained according to the procedures set forth in Example 3.

TABLE 6

K1C10_MOUSE
Keratin, type I cytoskeletal 10 OS = *Mus musculus* GN = Krt10 PE = 1 SV = 3
ALBU_MOUSE
Serum albumin OS = *Mus musculus* GN = Alb PE = 1 SV = 3
K2C75_MOUSE
Keratin, type II cytoskeletal 75 OS = *Mus musculus* GN = Krt75 PE = 1 SV = 1
K2C1_MOUSE
Keratin, type II cytoskeletal 1 OS = *Mus musculus* GN = Krt1 PE = 1 SV = 4
K1C14_MOUSE
Keratin, type I cytoskeletal 14 OS = *Mus musculus* GN = Krt14 PE = 1 SV = 2
K2C5_MOUSE
Keratin, type II cytoskeletal 5 OS = *Mus musculus* GN = Krt5 PE = 2 SV = 1
K1C15_MOUSE
Keratin, type I cytoskeletal 15 OS = *Mus musculus* GN = Krt15 PE = 1 SV = 2
K1C13_MOUSE
Keratin, type I cytoskeletal 13 OS = *Mus musculus* GN = Krt13 PE = 2 SV = 2
K2C6A_MOUSE
Keratin, type II cytoskeletal 6A OS = *Mus musculus* GN = Krt6a PE = 2 SV = 3
K2C4_MOUSE
Keratin, type II cytoskeletal 4 OS = *Mus musculus* GN = Krt4 PE = 2 SV = 2
K2C73_MOUSE
Keratin, type II cytoskeletal 73 OS = *Mus musculus* GN = Krt73 PE = 2 SV = 1
K1C17_MOUSE
Keratin, type I cytoskeletal 17 OS = *Mus musculus* GN = Krt17 PE = 1 SV = 3
K22O_MOUSE
Keratin, type II cytoskeletal 2 oral OS = *Mus musculus* GN = Krt76 PE = 2 SV = 1
K2C79_MOUSE
Keratin, type II cytoskeletal 79 OS = *Mus musculus* GN = Krt79 PE = 2 SV = 2
HBA_MOUSE
Hemoglobin subunit alpha OS = *Mus musculus* GN = Hba PE = 1 SV = 2
AATC_MOUSE
Aspartate aminotransferase, cytoplasmic OS = *Mus musculus* GN = Got1 PE = 1 SV = 2
K1C19_MOUSE
Keratin, type I cytoskeletal 19 OS = *Mus musculus* GN = Krt19 PE = 2 SV = 1
K1C42_MOUSE
Keratin, type I cytoskeletal 42 OS = *Mus musculus* GN = Krt42 PE = 1 SV = 1
K2C1B_MOUSE
Keratin, type II cytoskeletal 1b OS = *Mus musculus* GN = Krt77 PE = 1 SV = 1
K2C71_MOUSE
Keratin, type II cytoskeletal 71 OS = *Mus musculus* GN = Krt71 PE = 1 SV = 1
K2C74_MOUSE
Keratin, type II cytoskeletal 74 OS = *Mus musculus* GN = Krt74 PE = 2 SV = 1
K2C8_MOUSE
Keratin, type II cytoskeletal 8 OS = *Mus musculus* GN = Krt8 PE = 1 SV = 4
K1C27_MOUSE
Keratin, type I cytoskeletal 27 OS = *Mus musculus* GN = Krt27 PE = 1 SV = 1

TABLE 6-continued

K2C72_MOUSE
Keratin, type II cytoskeletal 72 OS = *Mus musculus* GN = Krt72 PE = 2 SV = 1
FABP4_MOUSE
Fatty acid-binding protein, adipocyte OS = *Mus musculus* GN = Fabp4 PE = 1 SV = 3
PTMS_MOUSE
Parathymosin OS = *Mus musculus* GN = Ptms PE = 2 SV = 3
K222P_MOUSE
Keratin-like protein KRT222 OS = *Mus musculus* GN = Krt222 PE = 2 SV = 1
K22E_MOUSE
Keratin, type II cytoskeletal 2 epidermal OS = *Mus musculus* GN = Krt2 PE = 1 SV = 1
HHB2_MOUSE
Hemoglobin subunit beta-2 OS = *Mus musculus* GN = Hbb-b2 PE = 1 SV = 2
TPIS_MOUSE
Triosephosphate isomerase OS = *Mus musculus* GN = Tpi1 PE = 1 SV = 3
FABPH_MOUSE
Fatty acid-binding protein, heart OS = *Mus musculus* GN = Fabp3 PE = 1 SV = 5
BICD2_MOUSE
Protein bicaudal D homolog 2 OS = *Mus musculus* GN = Bicd2 PE = 1 SV = 1
K2C1_PANTR
Keratin, type II cytoskeletal 1 OS = *Pan troglodytes* GN = KRT1 PE = 2 SV = 1
K2C1_HUMAN
Keratin, type II cytoskeletal 1 OS = *Homo sapiens* GN = KRT1 PE = 1 SV = 5
K1C9_HUMAN
Keratin, type I cytoskeletal 9 OS = *Homo sapiens* GN = KRT9 PE = 1 SV = 2
K22E_HUMAN
Keratin, type II cytoskeletal 2 epidermal OS = *Homo sapiens* GN = KRT2 PE = 1 SV = 1
K1C10_HUMAN
Keratin, type I cytoskeletal 10 OS = *Homo sapiens* GN = KRT10 PE = 1 SV = 4
K1C10_CANFA
Keratin, type I cytoskeletal 10 OS = *Canis familiaris* GN = KRT10 PE = 2 SV = 1
K2C1_RAT
Keratin, type II cytoskeletal 1 OS = *Rattus norvegicus* GN = Krt1 PE = 2 SV = 1
K22E_MOUSE
Keratin, type II cytoskeletal 2 epidermal OS = *Mus musculus* GN = Krt2 PE = 1 SV = 1
K1C14_HUMAN
Keratin, type I cytoskeletal 14 OS = *Homo sapiens* GN = KRT14 PE = 1 SV = 3
K1C10_BOVIN
Keratin, type I cytoskeletal 10 OS = *Bos taurus* GN = KRT10 PE = 3 SV = 1
K2C75_BOVIN
Keratin, type II cytoskeletal 75 OS = *Bos taurus* GN = KRT75 PE = 2 SV = 1
TRYP_PIG
Trypsin OS = *Sus scrofa* PE = 1 SV = 1
K2C75_RAT
Keratin, type II cytoskeletal 75 OS = *Rattus norvegicus* GN = Krt75 PE = 2 SV = 2
K2C6A_RAT
Keratin, type II cytoskeletal 6A OS = *Rattus norvegicus* GN = Krt6a PE = 1 SV = 1
ALBU_MOUSE
Serum albumin OS = *Mus musculus* GN = Alb PE = 1 SV = 3
K2C4_RAT
Keratin, type II cytoskeletal 4 OS = *Rattus norvegicus* GN = Krt4 PE = 2 SV = 1
K2C73_HUMAN
Keratin, type II cytoskeletal 73 OS = *Homo sapiens* GN = KRT73 PE = 1 SV = 1
K2C6A_HUMAN
Keratin, type II cytoskeletal 6A OS = *Homo sapiens* GN = KRT6A PE = 1 SV = 3
K2C73_MOUSE
Keratin, type II cytoskeletal 73 OS = *Mus musculus* GN = Krt73 PE = 2 SV = 1
K2C1B_MOUSE
Keratin, type II cytoskeletal 1b OS = *Mus musculus* GN = Krt77 PE = 1 SV = 1
K2C5_RAT
Keratin, type II cytoskeletal 5 OS = *Rattus norvegicus* GN = Krt5 PE = 1 SV = 1
K2C6A_MOUSE
Keratin, type II cytoskeletal 6A OS = *Mus musculus* GN = Krt6a PE = 2 SV = 3
K2C4_MOUSE
Keratin, type II cytoskeletal 4 OS = *Mus musculus* GN = Krt4 PE = 2 SV = 2
K2CO_MOUSE
Keratin, type II cytoskeletal 2 oral OS = *Mus musculus* GN = Krt76 PE = 2 SV = 1
K2C3_HUMAN
Keratin, type II cytoskeletal 3 OS = *Homo sapiens* GN = KRT3 PE = 1 SV = 2
K2C72_HUMAN
Keratin, type II cytoskeletal 72 OS = *Homo sapiens* GN = KRT72 PE = 1 SV = 2
HBD_TARSY
Hemoglobin subunit delta OS = *Tarsius syrichta* GN = HBD PE = 2 SV = 2
K1C13_MOUSE
Keratin, type I cytoskeletal 13 OS = *Mus musculus* GN = Krt13 PE = 2 SV = 2
HBA_CRIGA
Hemoglobin subunit alpha OS = *Cricetomys gambianus* GN = HBA PE = 1 SV = 2
TRY1_RAT
Anionic trypsin-1 OS = *Rattus norvegicus* GN = Prss1 PE = 1 SV = 1
K2C8_MOUSE
Keratin, type II cytoskeletal 8 OS = *Mus musculus* GN = Krt8 PE = 1 SV = 4

TABLE 6-continued

HBB_CALTO
Hemoglobin subunit beta OS = *Callicebus torquatus* GN = HBB PE = 2 SV = 3
K1C3_XENLA
Keratin, type I cytoskeletal 47 kDa (Fragment) OS = *Xenopus laevis* GN = xk81b1
PE = 3 SV = 2
K1C24_HUMAN
Keratin, type I cytoskeletal 24 OS = *Homo sapiens* GN = KRT24 PE = 1 SV = 1
K2C4_HUMAN
Keratin, type II cytoskeletal 4 OS = *Homo sapiens* GN = KRT4 PE = 1 SV = 4
AATC_HORSE
Aspartate aminotransferase, cytoplasmic OS = *Equus caballus* GN = GOT1 PE = 1 SV = 2
K1C16_HUMAN
Keratin, type I cytoskeletal 16 OS = *Homo sapiens* GN = KRT16 PE = 1 SV = 4
HBA_HUMAN
Hemoglobin subunit alpha OS = *Homo sapiens* GN = HBA1 PE = 1 SV = 2
HBA1_BUBBU
Hemoglobin subunit alpha-1 OS = *Bubalus bubalis* PE = 2 SV = 3
K1C42_RAT
Keratin, type I cytoskeletal 42 OS = *Rattus norvegicus* GN = Krt42 PE = 2 SV = 1
K1C14_CHICK
Keratin, type I cytoskeletal 14 OS = *Gallus gallus* GN = KRT14 PE = 2 SV = 1
HBA_MESAU
Hemoglobin subunit alpha OS = *Mesocricetus auratus* GN = HBA PE = 1 SV = 1
UP03_PINHA
Unknown protein 3 (Fragment) OS = *Pinus halepensis* PE = 1 SV = 1
IGH1M_MOUSE
Ig gamma-1 chain C region, membrane-bound form OS = *Mus musculus* GN = Ighg1
PE = 1 SV = 2
K2C5_PANTR
Keratin, type II cytoskeletal 5 OS = *Pan troglodytes* GN = KRT5 PE = 2 SV = 1
HBA_BISBO
Hemoglobin subunit alpha-I/II OS = *Bison bonasus* PE = 1 SV = 2
HBA_TALEU
Hemoglobin subunit alpha OS = *Talpa europaea* GN = HBA PE = 1 SV = 1
HIR3_CHAGB
Histone transcription regulator 3 homolog OS = *Chaetomium globosum* GN = HIR3
PE = 3 SV = 1
K1C10_HUMAN
Keratin, type I cytoskeletal 10 OS = *Homo sapiens* GN = KRT10 PE = 1 SV = 4
K22E_HUMAN
Keratin, type II cytoskeletal 2 epidermal OS = *Homo sapiens* GN = KRT2 PE = 1 SV = 1
K1C9_HUMAN
Keratin, type I cytoskeletal 9 OS = *Homo sapiens* GN = KRT9 PE = 1 SV = 2
K2C1_PANTR
Keratin, type II cytoskeletal 1 OS = *Pan troglodytes* GN = KRT1 PE = 2 SV = 1
K2C1_HUMAN
Keratin, type II cytoskeletal 1 OS = *Homo sapiens* GN = KRT1 PE = 1 SV = 5
K1C10_CANFA
Keratin, type I cytoskeletal 10 OS = *Canis familiaris* GN = KRT10 PE = 2 SV = 1
K1C14_HUMAN
Keratin, type I cytoskeletal 14 OS = *Homo sapiens* GN = KRT14 PE = 1 SV = 3
K2C5_PANTR
Keratin, type II cytoskeletal 5 OS = *Pan troglodytes* GN = KRT5 PE = 2 SV = 1
K2C6A_HUMAN
Keratin, type II cytoskeletal 6A OS = *Homo sapiens* GN = KRT6A PE = 1 SV = 3
K1C16_HUMAN
Keratin, type I cytoskeletal 16 OS = *Homo sapiens* GN = KRT16 PE = 1 SV = 4
TRYP_PIG
Trypsin OS = *Sus scrofa* PE = 1 SV = 1
K2C79_HUMAN
Keratin, type II cytoskeletal 79 OS = *Homo sapiens* GN = KRT79 PE = 1 SV = 1
K1C15_HUMAN
Keratin, type I cytoskeletal 15 OS = *Homo sapiens* GN = KRT15 PE = 1 SV = 2
K1C15_SHEEP
Keratin, type I cytoskeletal 15 OS = *Ovis aries* GN = KRT15 PE = 2 SV = 1
K1C10_BOVIN
Keratin, type I cytoskeletal 10 OS = *Bos taurus* GN = KRT10 PE = 3 SV = 1
K1C13_HUMAN
Keratin, type I cytoskeletal 13 OS = *Homo sapiens* GN = KRT13 PE = 1 SV = 3
K2CO_CHICK
Keratin, type II cytoskeletal cochleal OS = *Gallus gallus* PE = 2 SV = 1
K2C1_RAT
Keratin, type II cytoskeletal 1 OS = *Rattus norvegicus* GN = Krt1 PE = 2 SV = 1
K2C5_RAT
Keratin, type II cytoskeletal 5 OS = *Rattus norvegicus* GN = Krt5 PE = 1 SV = 1
K2C75_BOVIN
Keratin, type II cytoskeletal 75 OS = *Bos taurus* GN = KRT75 PE = 2 SV = 1
K2C7_BOVIN
Keratin, type II cytoskeletal 7 OS = *Bos taurus* GN = KRT7 PE = 2 SV = 1

TABLE 6-continued

K2C5_BOVIN
Keratin, type II cytoskeletal 5 OS = *Bos taurus* GN = KRT5 PE = 1 SV = 1
K2C6A_RAT
Keratin, type II cytoskeletal 6A OS = *Rattus norvegicus* GN = Krt6a PE = 1 SV = 1
K2C75_RAT
Keratin, type II cytoskeletal 75 OS = *Rattus norvegicus* GN = Krt75 PE = 2 SV = 2
K2C73_MOUSE
Keratin, type II cytoskeletal 73 OS = *Mus musculus* GN = Krt73 PE = 2 SV = 1
K22E_CANFA
Keratin, type II cytoskeletal 2 epidermal OS = *Canis familiaris* GN = KRT2 PE = 2
SV = 1
K2C4_RAT
Keratin, type II cytoskeletal 4 OS = *Rattus norvegicus* GN = Krt4 PE = 2 SV = 1
K1C3_XENLA
Keratin, type I cytoskeletal 47 kDa (Fragment) OS = *Xenopus laevis* GN = xk81b1
PE = 3 SV = 2
K22O_HUMAN
Keratin, type II cytoskeletal 2 oral OS = *Homo sapiens* GN = KRT76 PE = 1 SV = 1
K2C3_RABIT
Keratin, type II cytoskeletal 3 OS = *Oryctolagus cuniculus* GN = KRT3 PE = 2 SV = 1
K1C19_RAT
Keratin, type I cytoskeletal 19 OS = *Rattus norvegicus* GN = Krt19 PE = 1 SV = 2
ALBU_MOUSE
Serum albumin OS = *Mus musculus* GN = Alb PE = 1 SV = 3
K2C8_XENLA
Keratin, type II cytoskeletal 8 OS = *Xenopus laevis* PE = 2 SV = 1
K2C8_RAT
Keratin, type II cytoskeletal 8 OS = *Rattus norvegicus* GN = Krt8 PE = 1 SV = 3
K22O_MOUSE
Keratin, type II cytoskeletal 2 oral OS = *Mus musculus* GN = Krt76 PE = 2 SV = 1
K2C4_HUMAN
Keratin, type II cytoskeletal 4 OS = *Homo sapiens* GN = KRT4 PE = 1 SV = 4
TRY1_RAT
Anionic trypsin-1 OS = *Rattus norvegicus* GN = Prss1 PE = 1 SV = 1
K1C13_MOUSE
Keratin, type I cytoskeletal 13 OS = *Mus musculus* GN = Krt13 PE = 2 SV = 2
K2C4_MOUSE
Keratin, type II cytoskeletal 4 OS = *Mus musculus* GN = Krt4 PE = 2 SV = 2
K2C8_DANRE
Keratin, type II cytoskeletal 8 OS = *Danio rerio* GN = krt8 PE = 1 SV = 1
KRT85_MOUSE
Keratin, type II cuticular Hb5 OS = *Mus musculus* GN = Krt85 PE = 2 SV = 2
K2C80_SOVIN
Keratin, type II cytoskeletal 80 OS = *Bos taurus* GN = KRT80 PE = 2 SV = 1
K1C12_RABIT
Keratin, type I cytoskeletal 12 (Fragment) OS = *Oryctolagus cuniculus*
GN = KRT12 PE = 2 SV = 1
K1C12_RAT
Keratin, type I cytoskeletal 12 OS = *Rattus norvegicus* GN = Krt12 PE = 2 SV = 1
K2C1B_RAT
Keratin, type II cytoskeletal 1b OS = *Rattus norvegicus* GN = Krt77 PE = 2 SV = 1
K1C1_XENLA
Keratin, type I cytoskeletal 47 kDa OS = *Xenopus laevis* GN = xk81a1 PE = 2 SV = 1
K2C73_HUMAN
Keratin, type II cytoskeletal 73 OS = *Homo sapiens* GN = KRT73 PE = 1 SV = 1
K1C24_HUMAN
Keratin, type I cytoskeletal 24 OS = *Homo sapiens* GN = KRT24 PE = 1 SV = 1
K2C8_MOUSE
Keratin, type II cytoskeletal 8 OS = *Mus musculus* GN = Krt8 PE = 1 SV = 4
K2C78_HUMAN
Keratin, type II cytoskeletal 78 OS = *Homo sapiens* GN = KRT78 PE = 1 SV = 2
K2C72_HUMAN
Keratin, type II cytoskeletal 72 OS = *Homo sapiens* GN = KRT72 PE = 1 SV = 2
K2C72_MOUSE
Keratin, type II cytoskeletal 72 OS = *Mus musculus* GN = Krt72 PE = 2 SV = 1
UP01_PINHA
Unknown protein 1 (Fragment) OS = *Pinus halepensis* PE = 1 SV = 1
K22E_MOUSE
Keratin, type II cytoskeletal 2 epidermal OS = *Mus musculus* GN = Krt2 PE = 1 SV = 1
K1C14_CHICK
Keratin, type I cytoskeletal 14 OS = *Gallus gallus* GN = KRT14 PE = 2 SV = 1
K1C27_HUMAN
Keratin, type I cytoskeletal 27 OS = *Homo sapiens* GN = KRT27 PE = 1 SV = 1
UP03_PINHA
Unknown protein 3 (Fragment) OS = *Pinus halepensis* PE = 1 SV = 1
FDL30_ARATH
Putative F-box/FBD/LRR-repeat protein At5g22610 OS = *Arabidopsis thaliana*
GN = At5g22610 PE = 4 SV = 1
NDC80_CANAL
Probable kinetochore protein NDC80 OS = *Candida albicans* GN = NDC80 PE = 3 SV = 1

TABLE 6-continued

K1C10_HUMAN
Keratin, type I cytoskeletal 10 OS = *Homo sapiens* GN = KRT10 PE = 1 SV = 4
K22E_HUMAN
Keratin, type II cytoskeletal 2 epidermal OS = *Homo sapiens* GN = KRT2 PE = 1 SV = 1
K2C1_PANTR
Keratin, type II cytoskeletal 1 OS = *Pan troglodytes* GN = KRT1 PE = 2 SV = 1
K1C10_CANFA
Keratin, type I cytoskeletal 10 OS = *Canis familiaris* GN = KRT10 PE = 2 SV = 1
K1C9_HUMAN
Keratin, type I cytoskeletal 9 OS = *Homo sapiens* GN = KRT9 PE = 1 SV = 2
K2C1_HUMAN
Keratin, type II cytoskeletal 1 OS = *Homo sapiens* GN = KRT1 PE = 1 SV = 5
K2C75_BOVIN
Keratin, type II cytoskeletal 75 OS = *Bos taurus* GN = KRT75 PE = 2 SV = 1
K2C75_RAT
Keratin, type II cytoskeletal 75 OS = *Rattus norvegicus* GN = Krt75 PE = 2 SV = 2
K2C1_RAT
Keratin, type II cytoskeletal 1 OS = *Rattus norvegicus* GN = Krt1 PE = 2 SV = 1
K2C6A_RAT
Keratin, type II cytoskeletal 6A OS = *Rattus norvegicus* GN = Krt6a PE = 1 SV = 1
K2C6A_HUMAN
Keratin, type II cytoskeletal 6A OS = *Homo sapiens* GN = KRT6A PE = 1 SV = 3
K2C5_BOVIN
Keratin, type II cytoskeletal 5 OS = *Bos taurus* GN = KRT5 PE = 1 SV = 1
K2C5_MOUSE
Keratin, type II cytoskeletal 5 OS = *Mus musculus* GN = KrtS PE = 2 SV = 1
K2C6A_MOUSE
Keratin, type II cytoskeletal 6A OS = *Mus musculus* GN = Krt6a PE = 2 SV = 3
K2C79_BOVIN
Keratin, type II cytoskeletal 79 OS = *Bos taurus* GN = KRT79 PE = 2 SV = 1
ALBU_MOUSE
Serum albumin OS = *Mus musculus* GN = Alb PE = 1 SV = 3
K2C1_MOUSE
Keratin, type II cytoskeletal 1 OS = *Mus musculus* GN = Krt1 PE = 1 SV = 4
TRYP_PIG
Trypsin OS = *Sus scrofa* PE = 1 SV = 1
K1C10_BOVIN
Keratin, type I cytoskeletal 10 OS = *Bos taurus* GN = KRT10 PE = 3 SV = 1
K22E_MOUSE
Keratin, type II cytoskeletal 2 epidermal OS = *Mus musculus* GN = Krt2 PE = 1 SV = 1
HBA_SPAEH
Hemoglobin subunit alpha OS = *Spalax leucodon ehrenbergi* GN = HBA PE = 1 SV = 1
HBA_SPECI
Hemoglobin subunit alpha OS = *Spermophilus citellus* GN = HBA PE = 1 SV = 1
K2C73_MOUSE
Keratin, type II cytoskeletal 73 OS = *Mus musculus* GN = Krt73 PE = 2 SV = 1
K2C1B_MOUSE
Keratin, type II cytoskeletal 1b OS = *Mus musculus* GN = Krt77 PE = 1 SV = 1
K2C4_RAT
Keratin, type II cytoskeletal 4 OS = *Rattus norvegicus* GN = Krt4 PE = 2 SV = 1
K2C73_HUMAN
Keratin, type II cytoskeletal 73 OS = *Homo sapiens* GN = KRT73 PE = 1 SV = 1
K2C5_PANTR
Keratin, type II cytoskeletal 5 OS = *Pan troglodytes* GN = KRT5 PE = 2 SV = 1
TRY1_RAT
Anionic trypsin-1 OS = *Rattus norvegicus* GN = Prss1 PE = 1 SV = 1
K2C4_MOUSE
Keratin, type II cytoskeletal 4 OS = *Mus musculus* GN = Krt4 PE = 2 SV = 2
K2O_MOUSE
Keratin, type II cytoskeletal 2 oral OS = *Mus musculus* GN = Krt76 PE = 2 SV = 1
K2C3_HUMAN
Keratin, type II cytoskeletal 3 OS = *Homo sapiens* GN = KRT3 PE = 1 SV = 2
K2C72_HUMAN
Keratin, type II cytoskeletal 72 OS = *Homo sapiens* GN = KRT72 PE = 1 SV = 2
K2C72_MOUSE
Keratin, type II cytoskeletal 72 OS = *Mus musculus* GN = Krt72 PE = 2 SV = 1
HBA_MOUSE
Hemoglobin subunit alpha OS = *Mus musculus* GN = Hba PE = 1 SV = 2
K1C14_HUMAN
Keratin, type I cytoskeletal 14 OS = *Homo sapiens* GN = KRT14 PE = 1 SV = 3
K1C3_XENLA
Keratin, type I cytoskeletal 47 kDa (Fragment) OS = *Xenopus laevis* GN = xk81b1 PE = 3 SV = 2
K1C1_XENLA
Keratin, type I cytoskeletal 47 kDa OS = *Xenopus laevis* GN = xk81a1 PE = 2 SV = 1
K1C12_RABIT
Keratin, type I cytoskeletal 12 (Fragment) OS = *Oryctolagus cuniculus* GN = KRT12 PE = 2 SV = 1
K1C12_RAT
Keratin, type I cytoskeletal 12 OS = *Rattus norvegicus* GN = Krt12 PE = 2 SV = 1

TABLE 6-continued

K2C8_MOUSE
Keratin, type II cytoskeletal 8 OS = *Mus musculus* GN = Krt8 PE = 1 SV = 4
ALBU_FELCA
Serum albumin OS = *Felis silvestris catus* GN = ALB PE = 1 SV = 1
K2C4_HUMAN
Keratin, type II cytoskeletal 4 OS = *Homo sapiens* GN = KRT4 PE = 1 SV = 4
HBB_CALTO
Hemoglobin subunit beta OS = *Callicebus torquatus* GN = HBB PE = 2 SV = 3
K1C25_BOVIN
Keratin, type I cytoskeletal 25 OS = *Bos taurus* GN = KRT25 PE = 2 SV = 1
HBA_MESAU
Hemoglobin subunit alpha OS = *Mesocricetus auratus* GN = HBA PE = 1 SV = 1
K2C8_BOVIN
Keratin, type II cytoskeletal 8 OS = *Bos taurus* GN = KRT8 PE = 2 SV = 3
K2C8_RAT
Keratin, type II cytoskeletal 8 OS = *Rattus norvegicus* GN = Krt8 PE = 1 SV = 3
MATK_ADELA
Maturase K OS = *Adesmia lanata* GN = matK PE = 3 SV = 1
HBA_BISBO
Hemoglobin subunit alpha-I/II OS = *Bison bonasus* PE = 1 SV = 2
HBA_TALEU
Hemoglobin subunit alpha OS = *Talpa europaea* GN = HBA PE = 1 SV = 1
K1C10_HUMAN
Keratin, type I cytoskeletal 10 OS = *Homo sapiens* GN = KRT10 PE = 1 SV = 4
K1C9_HUMAN
Keratin, type I cytoskeletal 9 OS = *Homo sapiens* GN = KRT9 PE = 1 SV = 2
K1C10_CANFA
Keratin, type I cytoskeletal 10 OS = *Canis familiaris* GN = KRT10 PE = 2 SV = 1
K22E_HUMAN
Keratin, type II cytoskeletal 2 epidermal OS = *Homo sapiens* GN = KRT2 PE = 1 SV = 1
K2C1_HUMAN
Keratin, type II cytoskeletal 1 OS = *Homo sapiens* GN = KRT1 PE = 1 SV = 5
K2C1_PANTR
Keratin, type II cytoskeletal 1 OS = *Pan troglodytes* GN = KRT1 PE = 2 SV = 1
CASQ1_MOUSE
Calsequestrin-1 OS = *Mus musculus* GN = Casq1 PE = 2 SV = 2
K2C6A_HUMAN
Keratin, type II cytoskeletal 6A OS = *Homo sapiens* GN = KRT6A PE = 1 SV = 3
HBB_GORGO
Hemoglobin subunit beta OS = *Gorilla gorilla gorilla* GN = HBB PE = 1 SV = 2
K2C5_HUMAN
Keratin, type II cytoskeletal 5 OS = *Homo sapiens* GN = KRT5 PE = 1 SV = 3
K2C1_RAT
Keratin, type II cytoskeletal 1 OS = *Rattus norvegicus* GN = Krt1 PE = 2 SV = 1
K1C10_BOVIN
Keratin, type I cytoskeletal 10 OS = *Bos taurus* GN = KRT10 PE = 3 SV = 1
HBB_MELME
Hemoglobin subunit beta OS = *Meles meles* GN = HBB PE = 1 SV = 1
HBB_CALTO
Hemoglobin subunit beta OS = *Callicebus torquatus* GN = HBB PE = 2 SV = 3
HBA_HUMAN
Hemoglobin subunit alpha OS = *Homo sapiens* GN = HBA1 PE = 1 SV = 2
ALBU_RAT
Serum albumin OS = *Rattus norvegicus* GN = Alb PE = 1 SV = 2
ALBU_FELCA
Serum albumin OS = *Felis silvestris catus* GN = ALB PE = 1 SV = 1
K2C6A_RAT
Keratin, type II cytoskeletal 6A OS = *Rattus norvegicus* GN = Krt6a PE = 1 SV = 1
ALBU_HUMAN
Serum albumin OS = *Homo sapiens* GN = ALB PE = 1 SV = 2
TRYP_PIG
Trypsin OS = *Sus scrofa* PE = 1 SV = 1
K2C75_BOVIN
Keratin, type II cytoskeletal 75 OS = *Bos taurus* GN = KRT75 PE = 2 SV = 1
MLE1_HUMAN
Myosin light chain 1, skeletal muscle isoform OS = *Homo sapiens* GN = MYL1 PE = 1 SV = 3
ACTS_ATRMM
Actin, alpha skeletal muscle OS = *Atractaspis microlepidota microlepidota* GN = ACTA1 PE = 2 SV = 1
ACT2_MOLOC
Actin, muscle-type OS = *Molgula oculata* PE = 3 SV = 1
HBB_NASNA
Hemoglobin subunit beta OS = *Nasua nasua* GN = HBB PE = 1 SV = 1
HBB_CANFA
Hemoglobin subunit beta OS = *Canis familiaris* GN = HBB PE = 1 SV = 1
HBA_MESAU
Hemoglobin subunit alpha OS = *Mesocricetus auratus* GN = HBA PE = 1 SV = 1
K2C5_BOVIN
Keratin, type II cytoskeletal 5 OS = *Bos taurus* GN = KRT5 PE = 1 SV = 1

TABLE 6-continued

K2C6A_MOUSE
Keratin, type II cytoskeletal 6A OS = *Mus musculus* GN = Krt6a PE = 2 SV = 3
HBB_MACMU
Hemoglobin subunit beta OS = *Macaca mulatta* GN = HBB PE = 1 SV = 1
HBB_SAISC
Hemoglobin subunit beta OS = *Saimiri sciureus* GN = HBB PE = 1 SV = 2
TRY1_RAT
Anionic trypsin-1 OS = *Rattus norvegicus* GN = Prss1 PE = 1 SV = 1
K2C8_MOUSE
Keratin, type II cytoskeletal 8 OS = *Mus musculus* GN = Krt8 PE = 1 SV = 4
K2C1B_RAT
Keratin, type II cytoskeletal 1b OS = *Rattus norvegicus* GN = Krt77 PE = 2 SV = 1
MDHM_BOVIN
Malate dehydrogenase, mitochondrial OS = *Bos taurus* GN = MDH2 PE = 2 SV = 1
HBA_CRIGA
Hemoglobin subunit alpha OS = *Cricetomys gambianus* GN = HBA PE = 1 SV = 2
HBA_SPECI
Hemoglobin subunit alpha OS = *Spermophilus citellus* GN = HBA PE = 1 SV = 1
HBB_PAGLA
Hemoglobin subunit beta OS = *Paguma larvata* GN = HBB PE = 1 SV = 1
HBB_MYOVE
Hemoglobin subunit beta OS = *Myotis velifer* GN = HBB PE = 1 SV = 1
K1C1_XENLA
Keratin, type I cytoskeletal 47 kDa OS = *Xenopus laevis* GN = xk81a1 PE = 2 SV = 1
ACT18_DICDI
Actin-18 OS = *Dictyostelium discoideum* GN = act18 PE = 3 SV = 3
K1C24_HUMAN
Keratin, type I cytoskeletal 24 OS = *Homo sapiens* GN = KRT24 PE = 1 SV = 1
ACT1_ARTSX
Actin, clone 205 OS = *Artemia* sp. PE = 2 SV = 1
ACTC_BRAFL
Actin, cytoplasmic OS = *Branchiostoma floridae* PE = 2 SV = 1
ACTB3_FUGRU
Actin, cytoplasmic 3 OS = *Fugu rubripes* GN = actbc PE = 2 SV = 1
ACT_THELA
Actin OS = *Thermomyces lanuginosus* PE = 3 SV = 1
ACT1_SACKO
Actin-1 OS = *Saccoglossus kowalevskii* PE = 2 SV = 1
ACT1_LYTPI
Actin, cytoskeletal 1 OS = *Lytechinus pictus* PE = 2 SV = 1
ACTC_BRALA
Actin, cytoplasmic OS = *Branchiostoma lanceolatum* PE = 2 SV = 1
ACT_CANGA
Actin OS = *Candida glabrata* GN = ACT1 PE = 3 SV = 1
ACT1_KLULA
Actin OS = *Kluyveromyces lactis* GN = ACT PE = 3 SV = 2
ACT_PHARH
Actin OS = *Phaffia rhodozyma* PE = 3 SV = 1
ACT_CANAL
Actin OS = *Candida albicans* GN = ACT1 PE = 3 SV = 1
ACT_SCHPO
Actin OS = *Schizosaccharomyces pombe* GN = act1 PE = 1 SV = 1
ACTBL_HUMAN
Beta-actin-like protein 2 OS = *Homo sapiens* GN = ACTBL2 PE = 1 SV = 2
A26CA_HUMAN
ANKRD26-like family C member 1A OS = *Homo sapiens* GN = A26C1A PE = 1 SV = 3
K2C4_RAT
Keratin, type II cytoskeletal 4 OS = *Rattus norvegicus* GN = Krt4 PE = 2 SV = 1
K2C73_HUMAN
Keratin, type II cytoskeletal 73 OS = *Homo sapiens* GN = KRT73 PE = 1 SV = 1
HBA_MACFA
Hemoglobin subunit alpha-A/Q/R/T OS = *Macaca fascicularis* PE = 1 SV = 1
HED_GORGO
Hemoglobin subunit delta OS = *Gorilla gorilla gorilla* GN = HBD PE = 1 SV = 2
MDHM_YEAST
Malate dehydrogenase, mitochondrial OS = *Saccharomyces cerevisiae* GN = MDH1
PE = 1 SV = 2
HBA_LAMGL
Hemoglobin subunit alpha OS = *Lama glama* GN = HBA PE = 1 SV = 1
HBB_RABIT
Hemoglobin subunit beta-½ OS = *Oryctolagus cuniculus* GN = HBB1 PE = 1 SV = 2
HED_ELEMA
Hemoglobin subunit delta OS = *Elephas maximus* GN = HBD PE = 2 SV = 3
FIBB_HUMAN
Fibrinogen beta chain OS = *Homo sapiens* GN = FGB PE = 1 SV = 2
HED_COLPO
Hemoglobin subunit delta OS = *Colobus polykomos* GN = HBD PE = 2 SV = 2
K2C4_MOUSE
Keratin, type II cytoskeletal 4 OS = *Mus musculus* GN = Krt4 PE = 2 SV = 2

TABLE 6-continued

K22O_MOUSE
Keratin, type II cytoskeletal 2 oral OS = *Mus musculus* GN = Krt76 PE = 2 SV = 1
K2C3_RABIT
Keratin, type II cytoskeletal 3 OS = *Oryctolagus cuniculus* GN = KRT3 PE = 2 SV = 1
TPISA_DANRE
Triosephosphate isomerase A OS = *Danio rerio* GN = tpi1a PE = 2 SV = 1
TPISA_SPOR
Triosephosphate isomerase OS = *Aspergillus oryzae* GN = tpiA PE = 2 SV = 1
TPIS_HERAR
Triosephosphate isomerase OS = *Herminiimonas arsenicoxydans* GN = tpiA PE = 3 SV = 1
VIM4_XENLA
Vimentin-4 OS = *Xenopus laevis* GN = vim4 PE = 2 SV = 1
VIME_BOVIN
Vimentin OS = *Bos taurus* GN = VIM PE = 1 SV = 3
MATK_ADELA
Maturase K OS = *Adesmia lanata* GN = matK PE = 3 SV = 1
CASA1_BOVIN
Alpha-S1-casein OS = *Bos taurus* GN = CSN1S1 PE = 1 SV = 2
MLE1_CHICK
Myosin light chain 1, skeletal muscle isoform OS = *Gallus gallus* PE = 1 SV = 3
HBA_ARAAR
Hemoglobin subunit alpha-A OS = *Ara ararauna* GN = HBAA PE = 1 SV = 2
PYRB_AERHH
Aspartate carbamoyltransferase OS = *Aeromonas hydrophila* subsp. *hydrophila*
(strain ATCC 7966 / NCIB 9240) GN = pyrB PE = 3 SV = 2
ATPB_BOVIN
ATP synthase subunit beta, mitochondrial OS = *Bos taurus* GN = ATP5B PE = 1 SV = 2
Q8BGZ7_MOUSE
10 days neonate skin cDNA, RIKEN full-length enriched library,
clone: 4732475I03 product: CYTOKERATIN homolog (10 days neonate skin cDNA,
RIKEN full-length enriched library, clone: 4732468K03 product: CYTOKERATIN
TYPE II homolog) (6 days neonate skin cD
K2C1_MOUSE
Keratin, type II cytoskeletal 1 (Cytokeratin-1) (CK-1) (Keratin-1) (K1) (67
kDa cytokeratin). - *Mus musculus* (Mouse).
Q9D2K8_MOUSE
0 day neonate head cDNA, RIKEN full-length enriched library,
clone: 4833436C19 product: keratin complex 2, basic, gene 1, full insert
sequence. - *Mus musculus* (Mouse).
Q32P04_MOUSE
Krt2-5 protein (Fragment). - *Mus musculus* (Mouse).
K2C6A_MOUSE
Keratin, type II cytoskeletal 6A (Cytokeratin-6A) (CK 6A) (K6a keratin)
(Keratin-6 alpha) (mK6-alpha). - *Mus musculus* (Mouse).
Q80VP7_MOUSE
Hypothetical protein MGC54654. - *Mus musculus* (Mouse).
Q8BIS2_MOUSE
10 days neonate skin cDNA, RIKEN full-length enriched library,
clone: 4732456N10 product: similar to KERATIN, TYPE II CYTOSKELETAL 6D
(CYTOKERATIN 6D) (CK 6D) (K6D KERATIN). - *Mus musculus* (Mouse).
Q9CXH5_MOUSE
17 days embryo head cDNA, RIKEN full-length enriched library,
clone: 3300001P16 product: hemoglobin, beta adult major chain, full insert
sequence. - *Mus musculus* (Mouse).
KRMSE1
keratin, 59K type I cytoskeletal - mouse
Q6NXH9_MOUSE
Type II keratin Kb36. - *Mus musculus* (Mouse).
K2C1B_MOUSE
Keratin, type II cytoskeletal 1b (Type II keratin Kb39) (Embryonic type II
keratin-1). - *Mus musculus* (Mouse).
Q6IFZ9_MOUSE
Type II keratin Kb37. - *Mus musculus* (Mouse).
Q3TTY5_MOUSE
10 days neonate skin cDNA, RIKEN full-length enriched library,
clone: 4732404G19 product: keratin complex 2, basic, gene 17, full insert
sequence (10 days neonate skin cDNA, RIKEN full-length enriched library,
clone: 4732426A12 product: keratin complex
Q6IFT3_MOUSE
Keratin Kb40. - *Mus musculus* (Mouse).
Q3UV17_MOUSE
Adult female vagina cDNA, RIKEN full-length enriched library,
clone: 9930024P18 product: similar to Keratin 2p. - *Mus musculus* (Mouse).
I59009
epidermal keratin subunit II - mouse
HAMS
hemoglobin alpha chains - mouse
K2C4_MOUSE
Keratin, type II cytoskeletal 4 (Cytokeratin-4) (CK-4) (Keratin-4) (K4)
(Cytoskeletal 57 kDa keratin). - *Mus musculus* (Mouse).

TABLE 6-continued

Q6IME9_MOUSE
Type-II keratin Kb35. - *Mus musculus* (Mouse).
K2C8_MOUSE
Keratin, type II cytoskeletal 8 (Cytokeratin-8) (CK-8) (Keratin-8) (K8)
(Cytokeratin endo A). - *Mus musculus* (Mouse).
Q3TV03_MOUSE
Adult male stomach cDNA, RIKEN full-length enriched library,
clone: 2210414C06 product: albumin 1, full insert sequence. - *Mus musculus*
(Mouse).
Q9Z1R9_MOUSE
Trypsinogen 16 (Protease, serine, 1). - *Mus musculus* (Mouse).
JQ0028
cytokeratin 19 - mouse
Q2M1G8_MOUSE.
2410039E07Rik protein (Fragment). - *Mus musculus* (Mouse).
AAH11074
BC011074 NID: - *Mus musculus*
KRMSE1
keratin, 59K type I cytoskeletal - mouse
Q9CY54_MOUSE
13 days embryo liver cDNA, RIKEN full-length enriched library,
clone: 2500004H04 product: hemoglobin, beta adult major chain, full insert
sequence. - *Mus musculus* (Mouse).
HAMS
hemoglobin alpha chains - mouse
Q9CY06_MOUSE
13 days embryo liver cDNA, RIKEN full-length enriched library,
clone: 2510040P05 product: hemoglobin, beta adult major chain, full insert
sequence. - *Mus musculus* (Mouse).
AAH11074
BC011074 NID: - *Mus musculus*
HBMS
hemoglobin beta major chain - mouse
Q3TTY5_MOUSE
10 days neonate skin cDNA, RIKEN full-length enriched library,
clone: 4732404G19 product: keratin complex 2, basic, gene 17, full insert
sequence (10 days neonate skin cDNA, RIKEN full-length enriched library,
clone: 4732426A12 product: keratin complex
Q3UJH8_MOUSE
16 days embryo heart cDNA, RIKEN full-length enriched library,
clone: i920001F12 product: glutamate oxaloacetate transaminase 1, soluble,
full insert sequence. - *Mus musculus* (Mouse).
Q8BGZ7_MOUSE
10 days neonate skin cDNA, RIKEN full-length enriched library,
clone: 4732475I03 product: CYTOKERATIN homolog (10 days neonate skin cDNA,
RIKEN full-length enriched library, clone: 4732468K03 product: CYTOKERATIN
TYPE II homolog) (6 days neonate skin cD
K1C17_MOUSE
Keratin, type I cytoskeletal 17 (Cytokeratin-17) (CK-17) (Keratin-17)
(K17). - *Mus musculus* (Mouse).
Q9R0S6_MOUSE
Beta-1-globin (Fragment). - *Mus musculus* (Mouse).
K2C1_MOUSE
Keratin, type II cytoskeletal 1 (Cytokeratin-1) (CK-1) (Keratin-1) (K1) (67
kDa cytokeratin). - *Mus musculus* (Mouse).
Q9D2K8_MOUSE
0 day neonate head cDNA, RIKEN full-length enriched library,
clone: 4833436C19 product: keratin complex 2, basic, gene 1, full insert
sequence. - *Mus musculus* (Mouse).
A55682
keratin 13, type I cytoskeletal - mouse
Q32P04_MOUSE
Krt2-5 protein (Fragment). - *Mus musculus* (Mouse).
CAA33084
MMHFABP NID: - *Mus musculus*
Q80VP7_MOUSE
Hypothetical protein MGC54654. - *Mus musculus* (Mouse).
Q8BIS2_MOUSE
10 days neonate skin cDNA, RIKEN full-length enriched library,
clone: 4732456N10 product: similar to KERATIN, TYPE II CYTOSKELETAL 6D
(CYTOKERATIN 6D) (CK 6D) (K6D KERATIN). - *Mus musculus* (Mouse).
Q6NXH9_M
Type II keratin Kb36. - *Mus musculus* (Mouse).
OUSE
K1C15_MOUSE
Keratin, type I cytoskeletal 15 (Cytokeratin-15) (CK-15) (Keratin-15)
(K15). - *Mus musculus* (Mouse).
FABPH_MOUSE
Fatty acid-binding protein, heart (H-FABP) (Heart-type fatty acid- binding
protein) (Mammary-derived growth inhibitor) (MDGI). - *Mus musculus* (Mouse).

TABLE 6-continued

Q3UV17_MOUSE
Adult female vagina cDNA, RIKEN full-length enriched library,
clone: 9930024P18 product: similar to Keratin 2p. - *Mus musculus* (Mouse).
K2C4_MOUSE
Keratin, type II cytoskeletal 4 (Cytokeratin-4) (CK-4) (Keratin-4) (K4)
(Cytoskeletal 57 kDa keratin). - *Mus musculus* (Mouse).
Q6IME9_MOUSE
Type-II keratin Kb35. - *Mus musculus* (Mouse).
Q6IFT3_MOUSE
Keratin Kb40. - *Mus musculus* (Mouse).
Q8VCW2_MOUSE
RIKEN cDNA 4631426H08. - *Mus musculus* (Mouse).
Q2M1G8_MOUSE
2410039E07Rik protein (Fragment). - *Mus musculus* (Mouse).
FABPA_MO
Fatty acid-binding protein, adipocyte (AFABP) (Adipocyte lipid-binding
protein) (ALBP) (A-FABP) (P2 adipocyte protein) (Myelin P2 protein homolog)
(3T3-L1 lipid-binding protein) (422 protein) (P15).-
USE
*Mus musculus* (Mouse).
I59009
epidermal keratin subunit II - mouse
Q3TV03_MOUSE
Adult male stomach cDNA, RIKEN full-length enriched library,
clone: 2210414C06 product: albumin 1, full insert sequence. - *Mus musculus*
(Mouse).
DEMSMC
malate dehydrogenase (EC 1.1.1.37), cytosolic - mouse
JQ0028
cytokeratin 19 - mouse
Q3UDM1_MOUSE
Bone marrow macrophage cDNA, RIKEN full-length enriched library,
clone: G530119K21 product: ATP-binding cassette, sub-family C (CFTR/MRP),
member 1, full insert sequence. (Fragment). - *Mus musculus* (Mouse).
Q3UBW7_MOUSE
Bone marrow macrophage cDNA, RIKEN full-length enriched library,
clone: I830015F18 product: transferrin, full insert sequence. - *Mus musculus*
(Mouse).
K1C10_MOUSE
Keratin, type I cytoskeletal 10 OS = *Mus musculus* GN = Krt10 PE = 1 SV = 3
K2C75_MOUSE
Keratin, type II cytoskeletal 75 OS = *Mus musculus* GN = Krt75 PE = 1 SV = 1
ALBU_MOUSE
Serum albumin OS = *Mus musculus* GN-Alb PE = 1 SV = 3
K2C5_MOUSE
Keratin, type II cytoskeletal 5 OS = *Mus musculus* GN = Krt5 PE = 2 SV = 1
K2C1_MOUSE
Keratin, type II cytoskeletal 1 OS = *Mus musculus* GN = Krt1 PE = 1 SV = 4
K2C6A_MOUSE
Keratin, type II cytoskeletal 6A OS = *Mus musculus* GN = Krt6a PE = 2 SV = 3
K2C6B_MOUSE
Keratin, type II cytoskeletal 6B OS = *Mus musculus* GN-Krt6b PE = 2 SV = 3
K2C79_MOUSE
Keratin, type II cytoskeletal 79 OS = *Mus musculus* GN = Krt79 PE = 2 SV = 2
K1C13_MOUSE
Keratin, type I cytoskeletal 13 OS = *Mus musculus* GN = Krt13 PE = 2 SV = 2
AATC_MOUSE
Aspartate aminotransferase, cytoplasmic OS = *Mus musculus* GN = Got1 PE = 1 SV = 2
K1C14_MOUSE
Keratin, type I cytoskeletal 14 OS = *Mus musculus* GN-Krt14 PE = 1 SV = 2
K1C17_MOUSE
Keratin, type I cytoskeletal 17 OS = *Mus musculus* GN = Krt17 PE = 1 SV = 3
K2C73_MOUSE
Keratin, type II cytoskeletal 73 OS = *Mus musculus* GN = Krt73 PE = 2 SV = 1
HBB1_MOUSE
Hemoglobin subunit beta-1 OS = *Mus musculus* GN = Hbb-b1 PE = 1 SV = 2
K2C71_MOUSE
Keratin; type II cytoskeletal 71 OS = *Mus musculus* GN = Krt71 PE = 1 SV = 1
K2C4_MOUSE
Keratin, type II cytoskeletal 4 OS = *Mus musculus* GN = Krt4 PE = 2 SV = 2
K2O_MOUSE
Keratin, type II cytoskeletal 2 oral OS = *Mus musculus* GN = Krt76 PE = 2 SV = 1
K2C72_MOUSE
Keratin, type II cytoskeletal 72 OS = *Mus musculus* GN = Krt72 PE = 2 SV = 1
K2C8_MOUSE
Keratin, type II cytoskeletal 8 OS = *Mus musculus* GN = Krt8 PE = 1 SV = 4
FABPH_MOUSE
Fatty acid-binding protein, heart OS = *Mus musculus* GN = Fabp3 PE = 1 SV = 5
SOX1_MOUSE
SOX-1 protein OS = *Mus musculus* GN-Sox1 PE = 2 SV = 1

TABLE 6-continued

SPA3M_MOUSE
Serine protease inhibitor A3M OS = *Mus musculus* GN = Serpina3m PE = 1 SV = 1
TPIS_MOUSE
Triosephosphate isomerase OS = *Mus musculus* GN = Tpi1 PE = 1 SV = 3
K1C15_MOUSE
Keratin, type I cytoskeletal 15 OS = *Mus musculus* GN = Krt15 PE = 1 SV = 2
K1C16_MOUSE
Keratin, type I cytoskeletal 16 OS = *Mus musculus* GN = Krt16 PE = 1 SV = 3
K22E_MOUSE
Keratin, type II cytoskeletal 2 epidermal OS = *Mus musculus* GN = Krt2 PE = 1 SV = 1
DNJC1_MOUSE
DnaJ homolog subfamily C member 1 OS = *Mus musculus* GN = Dnajc1 PE = 1 SV = 1
HBA_MOUSE
Hemoglobin subunit alpha OS = *Mus musculus* GN = Hba PE = 1 SV = 2
ARVC_MOUSE
Armadillo repeat protein deleted in velo-cardio-facial syndrome homolog
OS = *Mus musculus* GN = Arvcf PE = 1 SV = 2
VIME_MOUSE
Vimentin OS = *Mus musculus* GN = Vim PE = 1 SV = 3
KRT83_MOUSE
Keratin, type II cuticular Hb3 OS = *Mus musculus* GN = Krt83 PE = 2 SV = 2
KRT82_MOUSE
Keratin, type II cuticular Hb2 OS = *Mus musculus* GN = Krt82 PE = 2 SV = 1
A1AT1_MOUSE
Alpha-l-antitrypsin 1-1 OS = *Mus musculus* GN = Serpina1a PE = 1 SV = 4
SODC_MOUSE
Superoxide dismutase [Cu-Zn] OS = *Mus musculus* GN = Sod1 PE = 1 SV = 2
AS250_MOUSE
250 kDa substrate of Akt OS = *Mus musculus* GN = Kiaa1272 PE = 1 SV = 2
K1C25_MOUSE
Keratin, type I cytoskeletal 25 OS = *Mus musculus* GN = Krt25 PE = 1 SV = 1
HBB1_MOUSE
Hemoglobin subunit beta-1 OS = *Mus musculus* GN = Hbb-b1 PE = 1 SV = 2
K1C10_MOUSE
Keratin, type I cytoskeletal 10 OS = *Mus musculus* GN = Krt10 PE = 1 SV = 3
K2C75_MOUSE
Keratin, type II cytoskeletal 75 OS = *Mus musculus* GN = Krt75 PE = 1 SV = 1
K2C1_MOUSE
Keratin, type II cytoskeletal 1 OS = *Mus musculus* GN = Krt1 PE = 1 SV = 4
K2C5_MOUSE
Keratin, type II cytoskeletal 5 OS = *Mus musculus* GN = Krt5 PE = 2 SV = 1
ALBU_MOUSE
Serum albumin OS = *Mus musculus* GN-Alb PE = 1 SV = 3
K2C79_MOUSE
Keratin, type II cytoskeletal 79 OS = *Mus musculus* GN = Krt79 PE = 2 SV = 2
K1C42_MOUSE
Keratin, type I cytoskeletal 42 OS = *Mus musculus* GN = Krt42 PE = 1 SV = 1
HBA_MOUSE
Hemoglobin subunit alpha OS = *Mus musculus* GN = Hba PE = 1 SV = 2
K2C73_MOUSE
Keratin, type II cytoskeletal 73 OS = *Mus musculus* GN = Krt73 PE = 2 SV = 1
K1C15_MOUSE
Keratin, type I cytoskeletal 15 OS = *Mus musculus* GN = Krt15 PE = 1 SV = 2
K2C1B_MOUSE
Keratin, type II cytoskeletal 1b OS = *Mus musculus* GN = Krt77 PE = 1 SV = 1
K1C27_MOUSE
Keratin, type I cytoskeletal 27 OS = *Mus musculus* GN = Krt27 PE = 1 SV = 1
K2C4_MOUSE
Keratin; type II cytoskeletal 4 OS = *Mus musculus* GN = Krt4 PE = 2 SV = 2
K2O_MOUSE
Keratin, type II cytoskeletal 2 oral OS = *Mus musculus* GN = Krt76 PE = 2 SV = 1
K2C72_MOUSE
Keratin, type II cytoskeletal 72 OS = *Mus musculus* GN = Krt72 PE = 2 SV = 1
K1C19_MOUSE
Keratin, type I cytoskeletal 19 OS = *Mus musculus* GN = Krt19 PE = 2 SV = 1
K1C17_MOUSE
Keratin, type I cytoskeletal 17 OS = *Mus musculus* GN = Krt17 PE = 1 SV = 3
K22E_MOUSE
Keratin, type II cytoskeletal 2 epidermal OS = *Mus musculus* GN = Krt2 PE = 1 SV = 1
SYTC_MOUSE
Threonyl-tRNA synthetase, cytoplasmic OS = *Mus musculus* GN = Tars PE = 1 SV = 2
HBE_MOUSE
Hemoglobin subunit epsilon-Y2 OS = *Mus musculus* GN = Hbb-y PE = 1 SV = 2
FTSJ2_MOUSE
FtsJ methyltransferase domain-containing protein 2 OS = *Mus musculus*
GN = Ftsjd2 PE = 1 SV = 1
DPOLA_MOUSE
DNA polymerase alpha catalytic subunit OS = *Mus musculus* GN = Pola1 PE = 1 SV = 2
HBB1_MOUSE Mass: 15830 Score: 216 Queries matched: 10 emPAI: 2.
Hemoglobin subunit beta-1 OS = *Mus musculus* GN = Hbb-b1 PE = 1 SV = 2

TABLE 6-continued

Check to include this hit in error tolerant search or archive report
HAMS
hemoglobin alpha chains - mouse
Q9CY12_MOUSE
13 days-embryo liver cDNA, RIKEN full-length enriched library,
clone: 2510039D09 product: hemoglobin, beta adult major chain, full insert
sequence. - *Mus musculus* (Mouse).
Q8BGZ7_MOUSE
10 days neonate skin cDNA, RIKEN full-length enriched library,
clone: 4732475I03 product: CYTOKERATIN homolog (10 days neonate skin cDNA,
RIKEN full-length enriched library, clone: 4732468K03 product: CYTOKERATIN
TYPE II homolog) (6 days neonate skin cD
Q32P04_MOUSE
Krt2-5 protein (Fragment). - *Mus musculus* (Mouse).
Q3TV03_MOUSE
Adult male stomach cDNA, RIKEN full-length enriched library,
clone: 2210414C06 product: albumin 1, full insert sequence. - *Mus musculus*
(Mouse).
KRMSE1
keratin, 59K type I cytoskeletal - mouse
K1C15_MOUSE
Keratin, type I cytoskeletal 15 (Cytokeratin-15) (CK-15) (Keratin-15)
(K15). - *Mus musculus* (Mouse).
Q8BIS2_MOUSE
10 days neonate skin cDNA, RIKEN full-length enriched library,
clone: 4732456N10 product: similar to KERATIN, TYPE II CYTOSKELETAL 6D
(CYTOKERATIN 6D) (CK 6D) (K6D KERATIN). - *Mus musculus* (Mouse).
Q8BGZ7_MOUSE
10 days neonate skin cDNA, RIKEN full-length enriched library,
clone: 4732475I03 product: CYTOKERATIN homolog (10 days neonate skin cDNA,
RIKEN full-length enriched library, clone: 4732468K03 product: CYTOKERATIN
TYPE II homolog) (6 days neonate skin cD
K2C6A_MOUSE
Keratin, type II cytoskeletal 6A (Cytokeratin-6A). (CK 6A) (K6a keratin)
(Keratin-6 alpha) (mK6-alpha). - *Mus musculus* (Mouse).
Q32P04_MOUSE
Krt2-5 protein (Fragment). - *Mus musculus* (Mouse).
Q8K2E4_MOUSE
CDNA sequence BC031593. - *Mus musculus* (Mouse).
K2C1_MOUSE
Keratin, type II cytoskeletal 1 (Cytokeratin-1) (CK-1) (Keratin-1) (K1) (67
kDa cytokeratin). - *Mus musculus* (Mouse).
Q9D2K8_MOUSE
0 day neonate head cDNA, RIKEN full-length enriched library,
clone: 4833436C19 product: keratin complex 2, basic, gene 1, full insert
sequence. - *Mus musculus* (Mouse).
Q8BIS2_MOUSE
10 days neonate skin cDNA, RIKEN full-length enriched library,
clone: 4732456N10 product: similar to KERATIN, TYPE II CYTOSKELETAL 6D
(CYTOKERATIN 6D) (CK 6D) (K6D KERATIN). - *Mus musculus* (Mouse).
Q80VP7_MOUSE
Hypothetical protein MGC54654. - *Mus musculus* (Mouse).
Q6NXH9_MOUSE
Type II keratin Kb36. - *Mus musculus* (Mouse).
Q6IFT3_MO
Keratin Kb40. - *Mus musculus* (Mouse).
USE
K2C1B_MOUSE
Keratin, type II cytoskeletal 1b (Type II keratin Kb39) (Embryonic type II
keratin-1). - *Mus musculus* (Mouse).
Q3UV17_MOUSE
Adult female vagina cDNA, RIKEN full-length enriched library,
clone: 9930024P18 product: similar to Keratin 2p. - *Mus musculus* (Mouse).
K2C4_MOUSE
Keratin, type II cytoskeletal 4 (Cytokeratin-4) (CK-4) (Keratin-4) (K4)
(Cytoskeletal 57 kDa keratin). - *Mus musculus* (Mouse).
AAH11074
BC011074 NID: - *Mus musculus*
BAA85657
AB033744 NID: - *Mus musculus*
Q6IFZ9_MOUSE
Type II keratin Kb37. - *Mus musculus* (Mouse).
159009
epidermal keratin subunit II - mouse
K1C17_MOUSE
Keratin, type I cytoskeletal 17 (Cytokeratin-17) (CK-17) (Keratin-17)
(K17). - *Mus musculus* (Mouse).
Q6IFX2_MOUSE
Type I keratin KA22. - *Mus musculus* (Mouse).

TABLE 6-continued

Q6IME9_MOUSE
Type-II keratin Kb35. - *Mus musculus* (Mouse).
BAE40567
AK168726 NID: - *Mus musculus*
AAD01692
AF021836 NID: - *Mus musculus*
Q3USS4
Adult male corpora quadrigemina cDNA, RIKEN full-length enriched library,
clone: B230315D14 product: glial fibrillary acidic protein, full insert
sequence. - *Mus musculus* (Mouse).
_MOUSE
Q3TTY5_MOUSE
10 days neonate skin cDNA, RIKEN full-length enriched library,
clone: 4732404G19 product: keratin complex 2, basic, gene 17, full insert
sequence (10 days neonate skin cDNA, RIKEN full-length enriched library,
clone: 4732426A12 product: keratin complex
K1C15_MOUSE
Keratin, type I cytoskeletal 15 (Cytokeratin-15) (CK-15) (Keratin-15)
(K15). - *Mus musculus* (Mouse).
Q3TWV0_MOUSE
Osteoclast-like cell cDNA, RIKEN full-length enriched library,
clone: 1420023H06 product: vimentin, full insert sequence. - *Mus musculus*
(Mouse).
Q9JKB4_MOUSE
Epidermal keratin 10 (Fragment). - *Mus musculus* (Mouse).
Q8VCW2_MOUSE
RIKEN cDNA 4631426H08. - *Mus musculus* (Mouse).
JQ0028
cytokeratin 19 - mouse
KRMSE1
keratin, 59K type I cytoskeletal - mouse
JC4030
DnaJ-like protein MTJ1 - mouse
E2AK4_MOUSE
Eukaryotic translation initiation factor 2-alpha kinase 4 (EC 2.7.11.1)
(GCN2-like protein) (mGCN2). - *Mus musculus* (Mouse).
BAB27580
AK011380 NID: - *Mus musculus*

I claim:

1. A method of quantifying the amount of ionizing radiation to which an individual has been exposed comprising determining the presence of one or more radiation associated markers.

2. A method according to claim 1 wherein the sample is selected from the group consisting of a buccal swab, saliva, plasma, serum, urine and blood.

3. A method according to claim 1 wherein determining the presence of one or more radiation associated markers in a sample is performed by Matrix assisted laser desorption ionization (MALDI) mass spectrometry.

4. A method according to claim 1 wherein determining the presence of one or more radiation associated markers in a sample is performed by (a) contacting the sample with an antibody which specifically binds to a radiation associated marker permitting formation of a complex between the antibody and the radiation associated marker; and (b) measuring the amount of complexes formed, thereby determining the amount of the radiation associated marker in the sample.

5. A method according to claim 4 further comprising (c) comparing the amount of radiation associated marker in the sample determined in step (b) with either (i) the amount determined for temporally matched, normal samples or (ii) the amount determined for samples obtained from individuals who have not been exposed to elevated levels of ionizing radiation.

* * * * *